United States Patent
Yoo

(10) Patent No.: US 11,839,444 B2
(45) Date of Patent: Dec. 12, 2023

(54) CEILING AI HEALTH MONITORING APPARATUS AND REMOTE MEDICAL-DIAGNOSIS METHOD USING THE SAME

(71) Applicant: RESEARCH & BUSINESS FOUNDATION SUNGKYUNKWAN UNIVERSITY, Suwon-si (KR)

(72) Inventor: Jae-Chern Yoo, Suwon-si (KR)

(73) Assignee: Research & Business Foundation Sungkyunkwan University, Suwon-si (KR)

(*) Notice: Subject to any disclaimer, the term of this patent is extended or adjusted under 35 U.S.C. 154(b) by 408 days.

(21) Appl. No.: 17/184,698

(22) Filed: Feb. 25, 2021

(65) Prior Publication Data

US 2022/0047160 A1 Feb. 17, 2022

(30) Foreign Application Priority Data

May 8, 2020 (KR) .................. 10-2020-0055019

(51) Int. Cl.
*A61B 5/00* (2006.01)
*G16H 80/00* (2018.01)
*A61B 5/01* (2006.01)
*G16H 50/20* (2018.01)

(52) U.S. Cl.
CPC ............ *A61B 5/0002* (2013.01); *A61B 5/015* (2013.01); *G16H 50/20* (2018.01); *G16H 80/00* (2018.01)

(58) Field of Classification Search
CPC ..... A61B 5/0002; A61B 5/015; A61B 5/0064; A61B 5/0823; A61B 5/4803; A61B 5/6889; G16H 50/20; G16H 80/00
See application file for complete search history.

(56) References Cited

U.S. PATENT DOCUMENTS

| 2018/0055384 A1* | 3/2018 | Ambili ................... G16H 40/63 |
| 2019/0205655 A1* | 7/2019 | Matsuoka .............. G06V 20/52 |
| 2019/0279481 A1* | 9/2019 | Silberschatz ...... G08B 21/0208 |

FOREIGN PATENT DOCUMENTS

| KR | 20-2017-0004039 U | 11/2017 |
| KR | 10-2018-0111098 A | 10/2018 |
| KR | 10-2019-0068522 A | 6/2019 |
| KR | 10-2019-0071724 A | 6/2019 |

* cited by examiner

*Primary Examiner* — Carl H Layno
*Assistant Examiner* — Aya Ziad Bakkar
(74) *Attorney, Agent, or Firm* — NSIP Law

(57) ABSTRACT

A ceiling artificial intelligence (AI) health monitoring system, includes a monitoring device provided on a ceiling of a space to acquire health information from a patient, and a medical management device configured to apply the health information of the patient acquired to an artificial intelligence-based learning model to determine health condition information of the patient and provide the determination result to a doctor monitor. The medical management device is configured to provide remote medical diagnosis information from the doctor monitor to a user terminal.

10 Claims, 13 Drawing Sheets

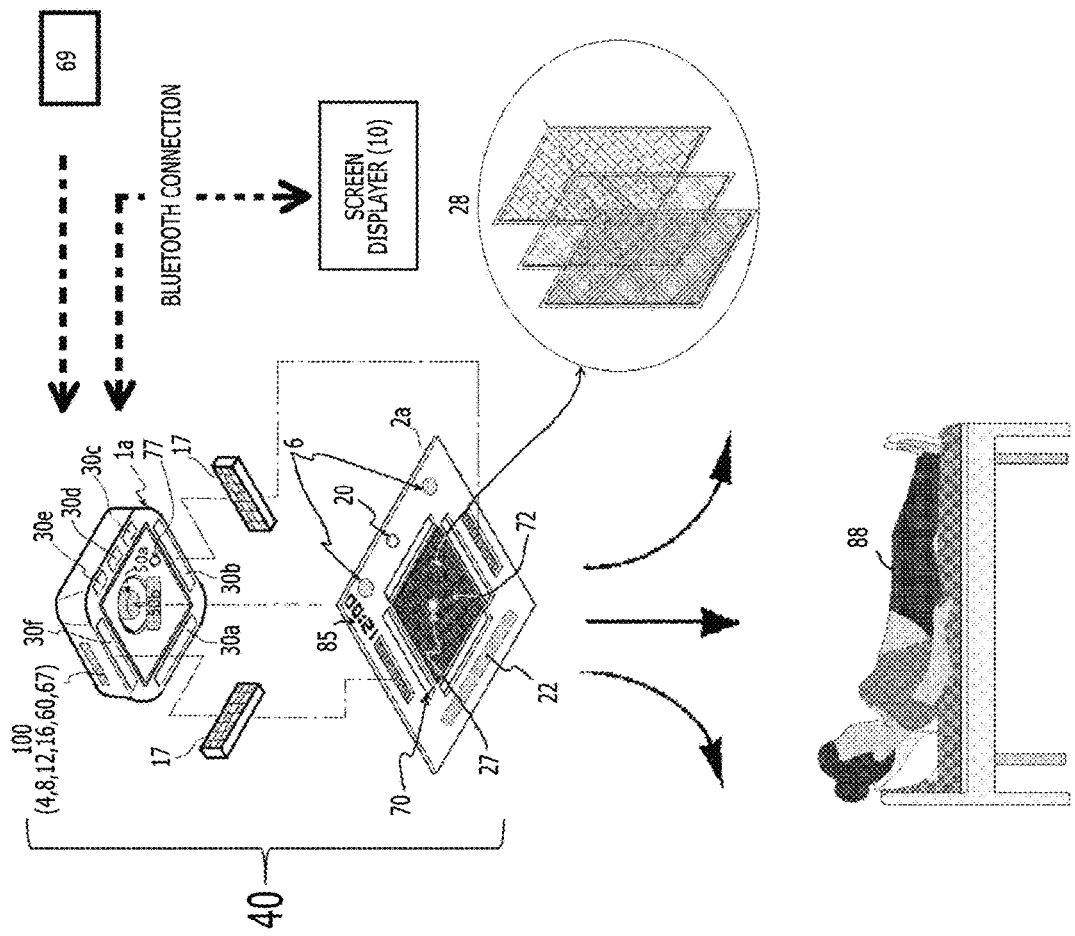

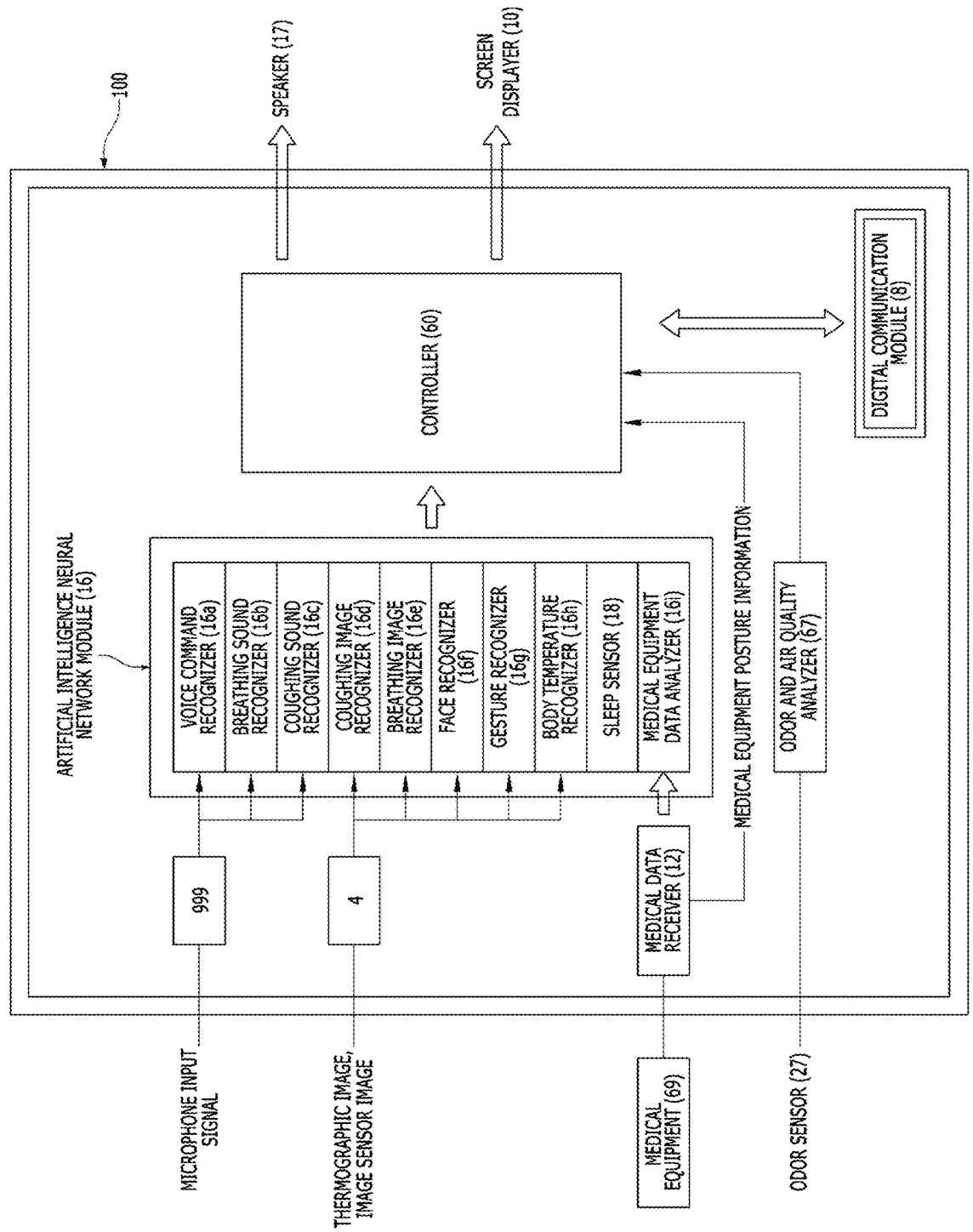

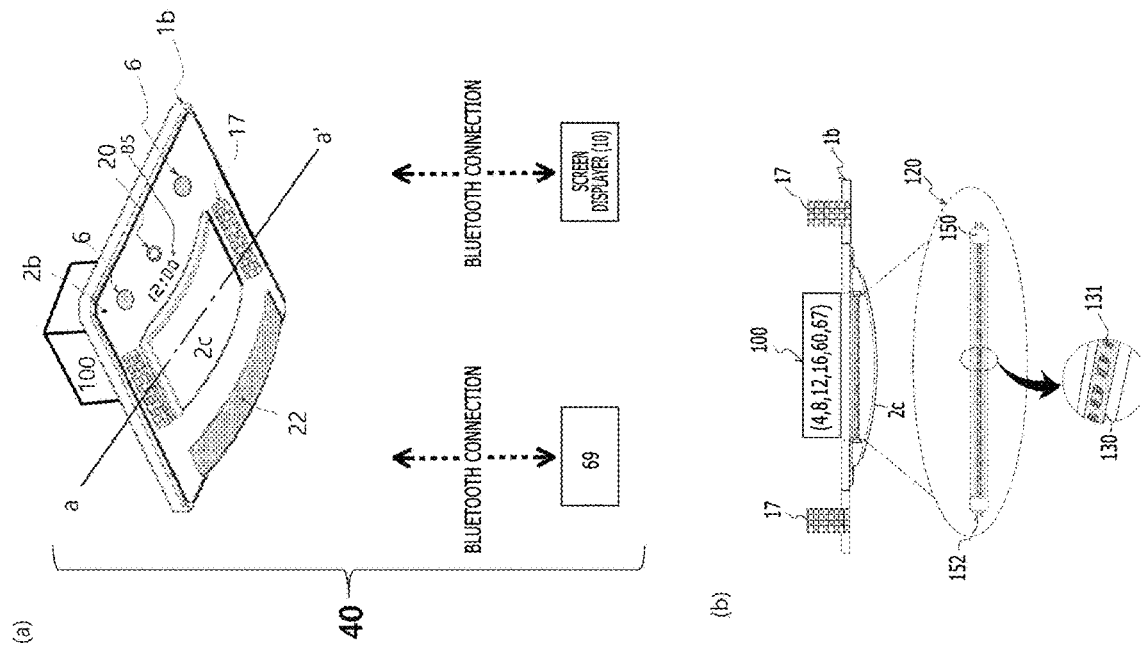

[FIG. 4A]
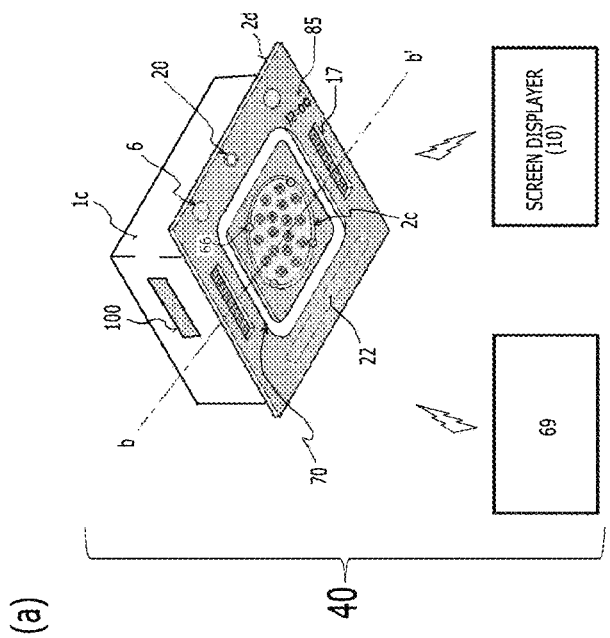
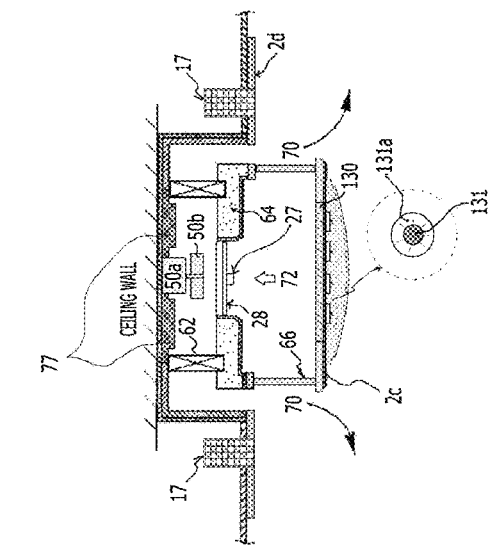

[FIG. 4B]
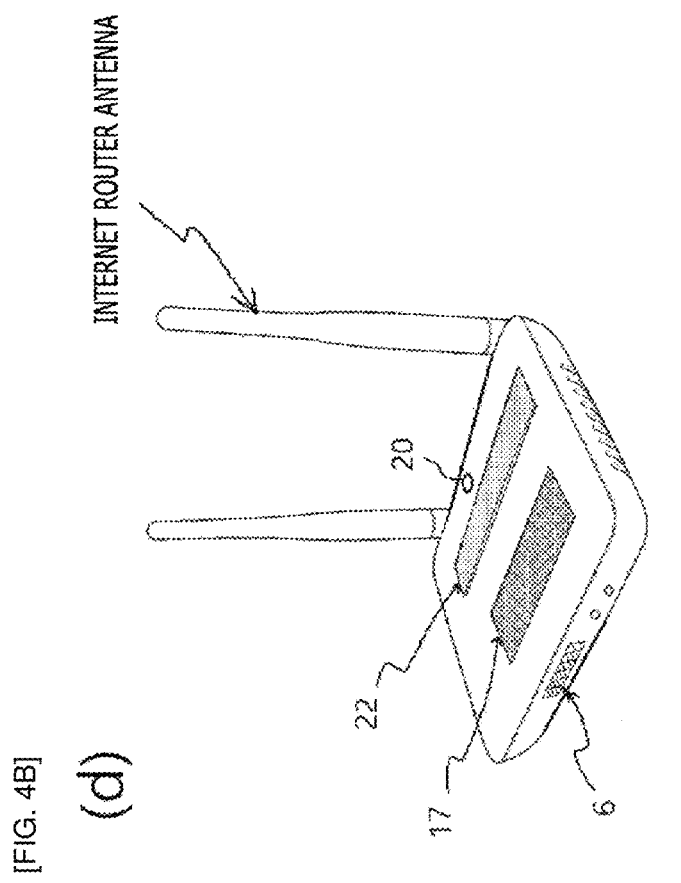
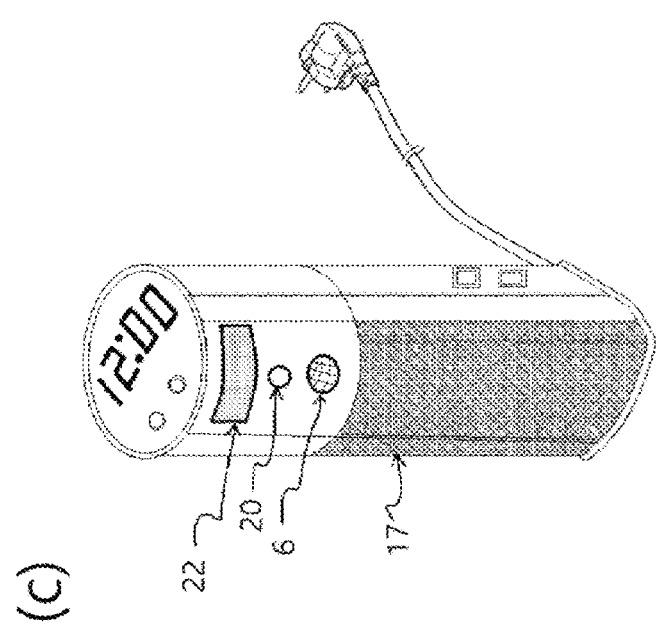

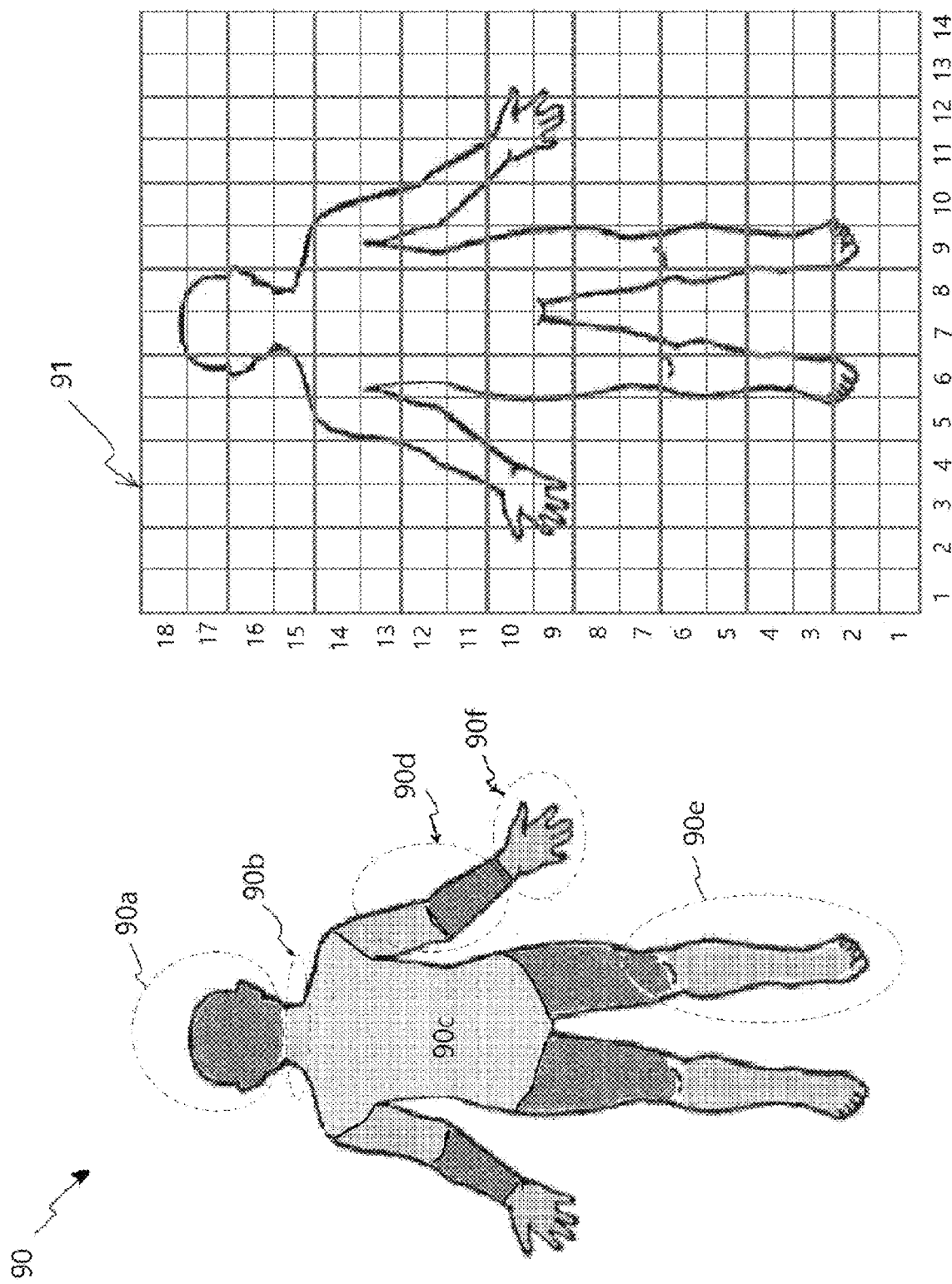

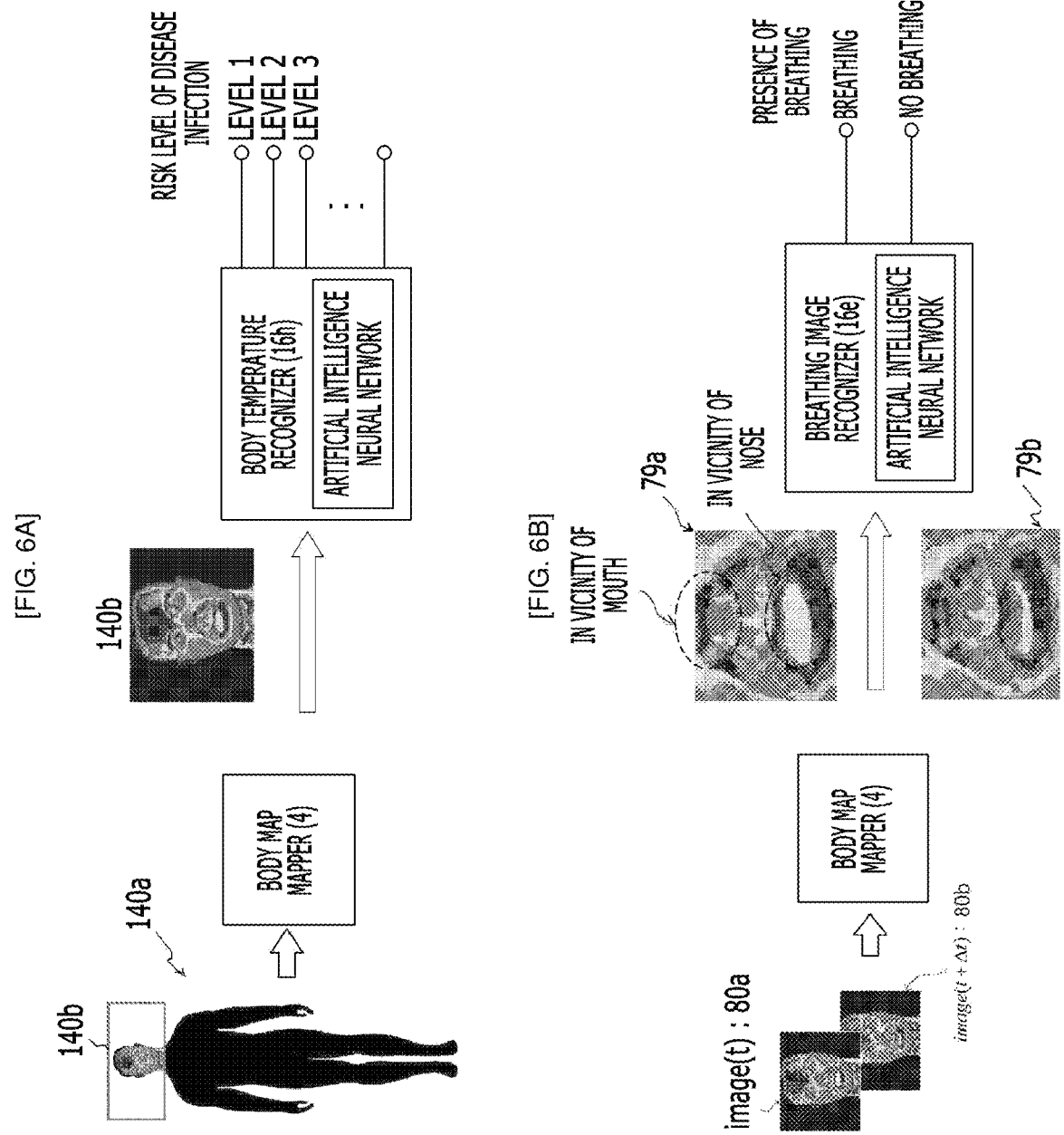

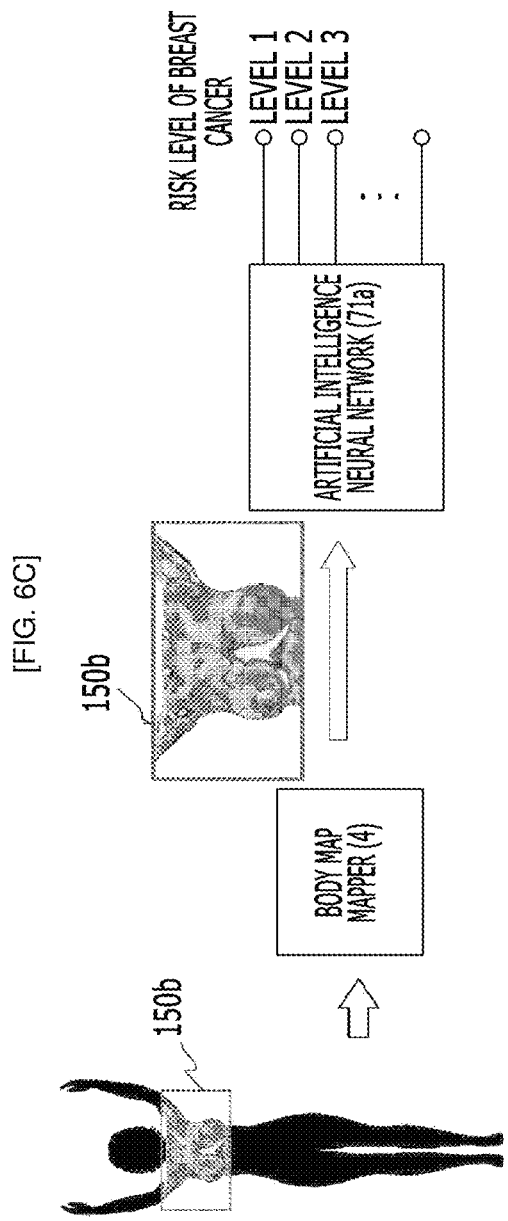

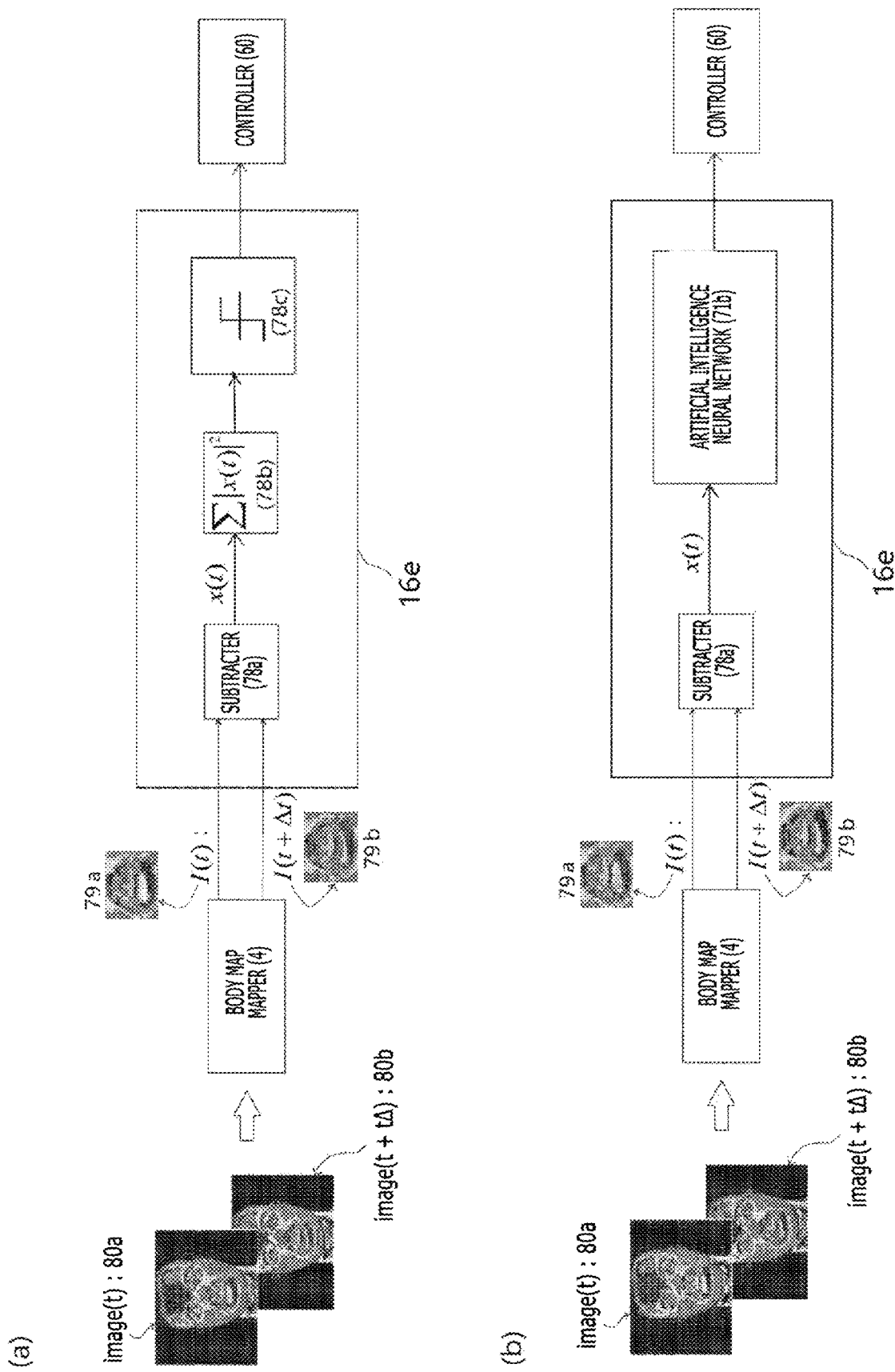
[FIG. 7]

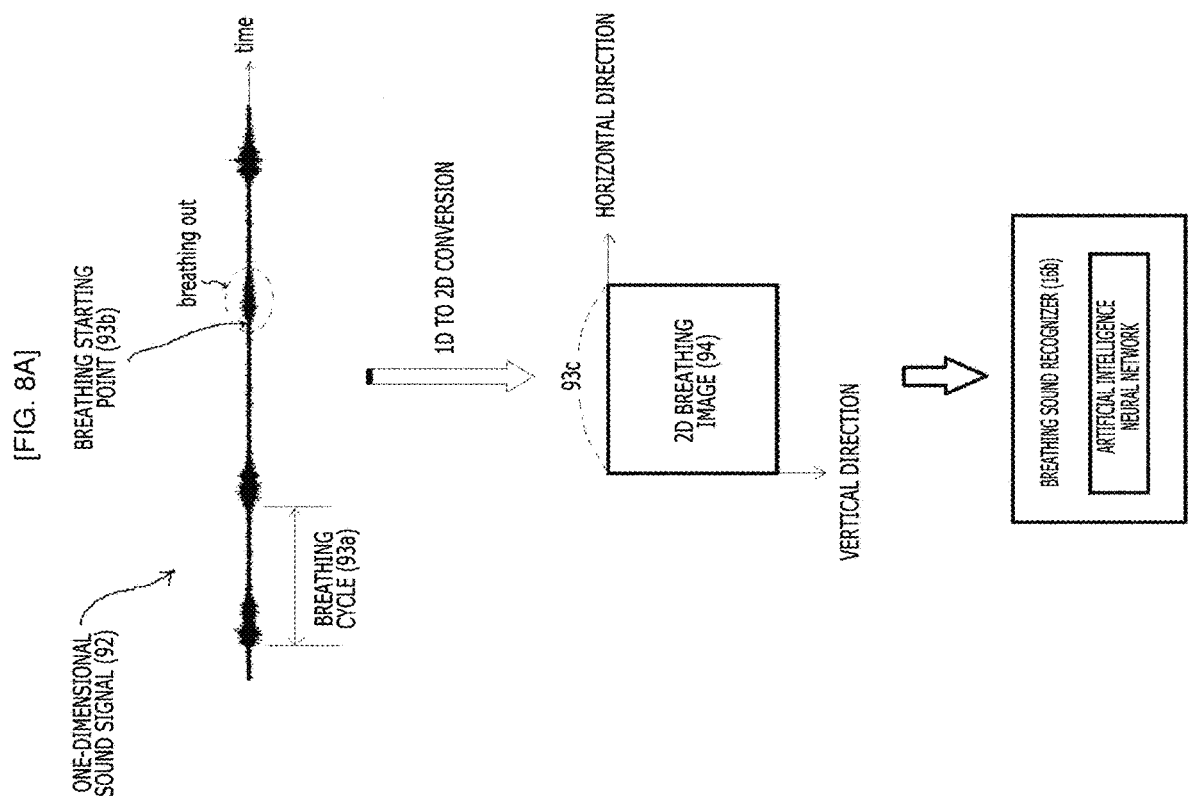

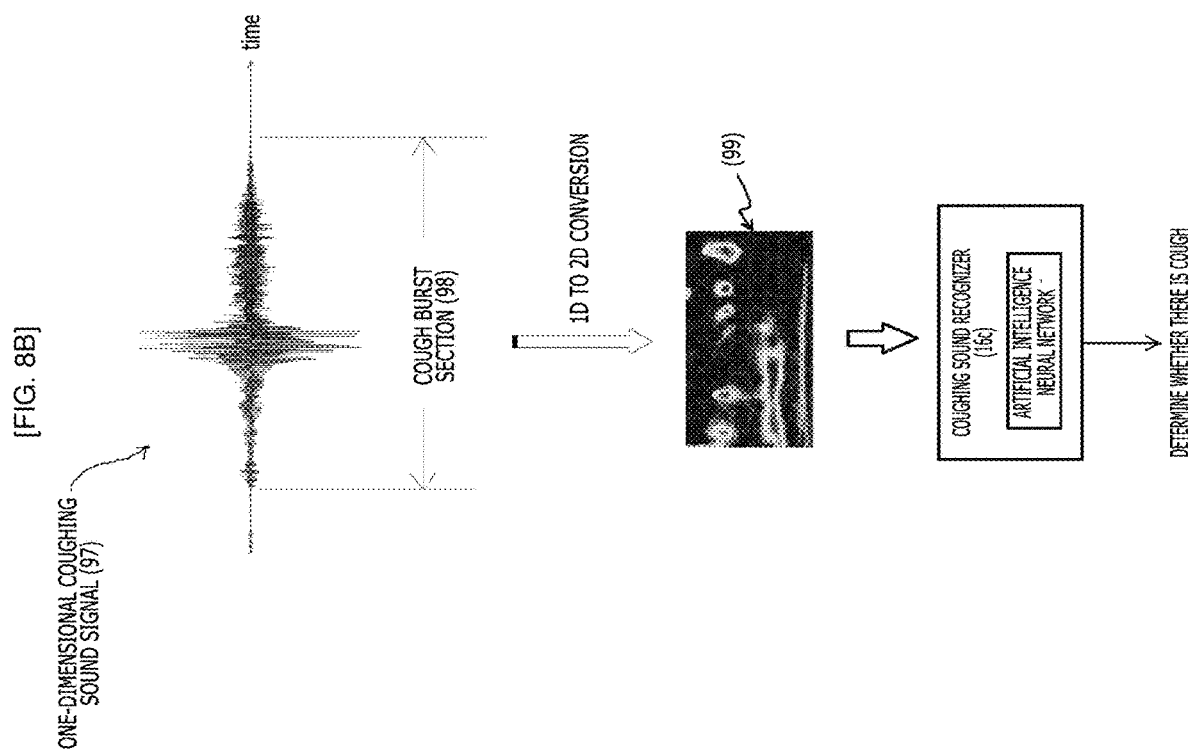

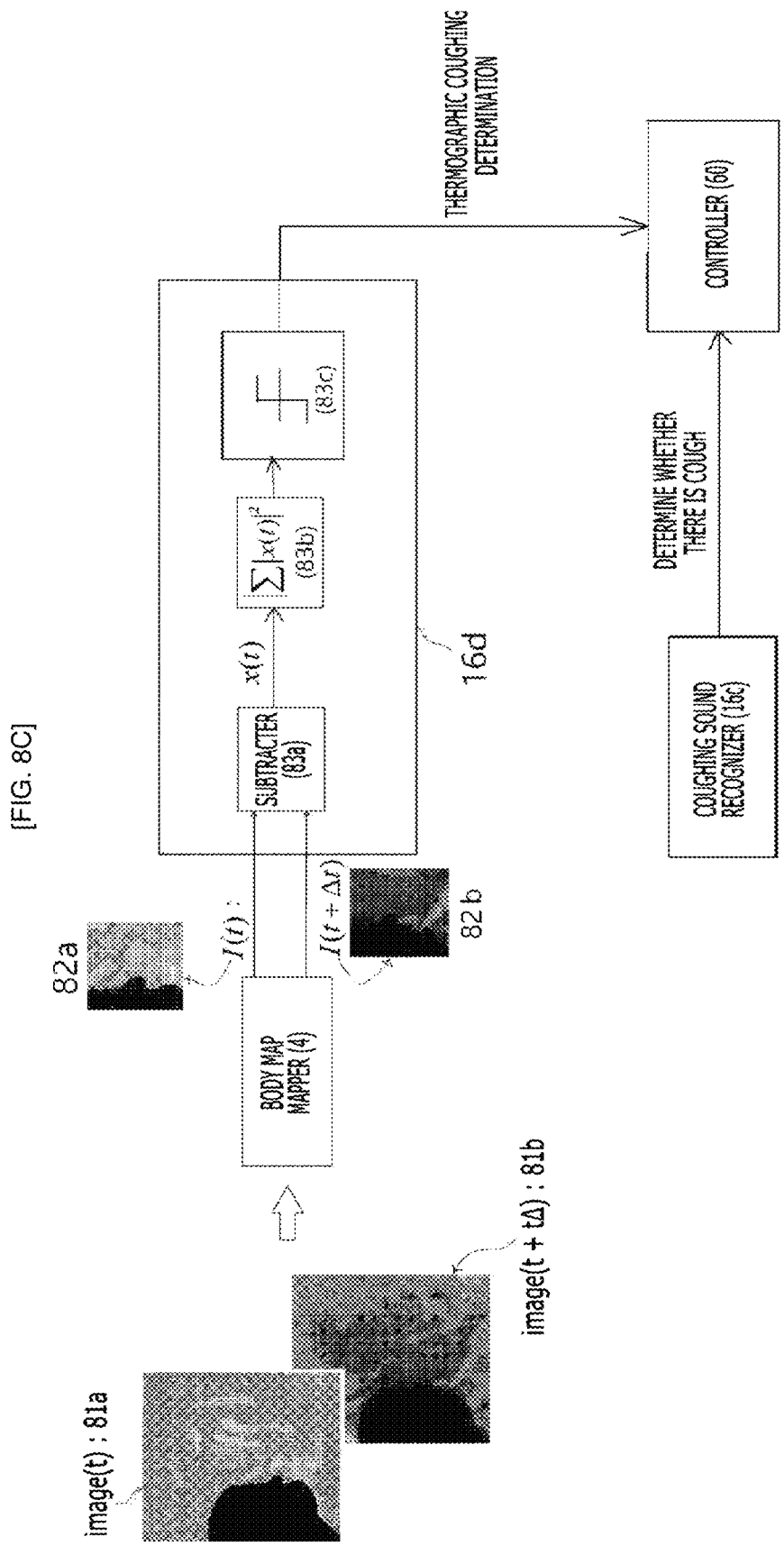
[FIG. 8C]

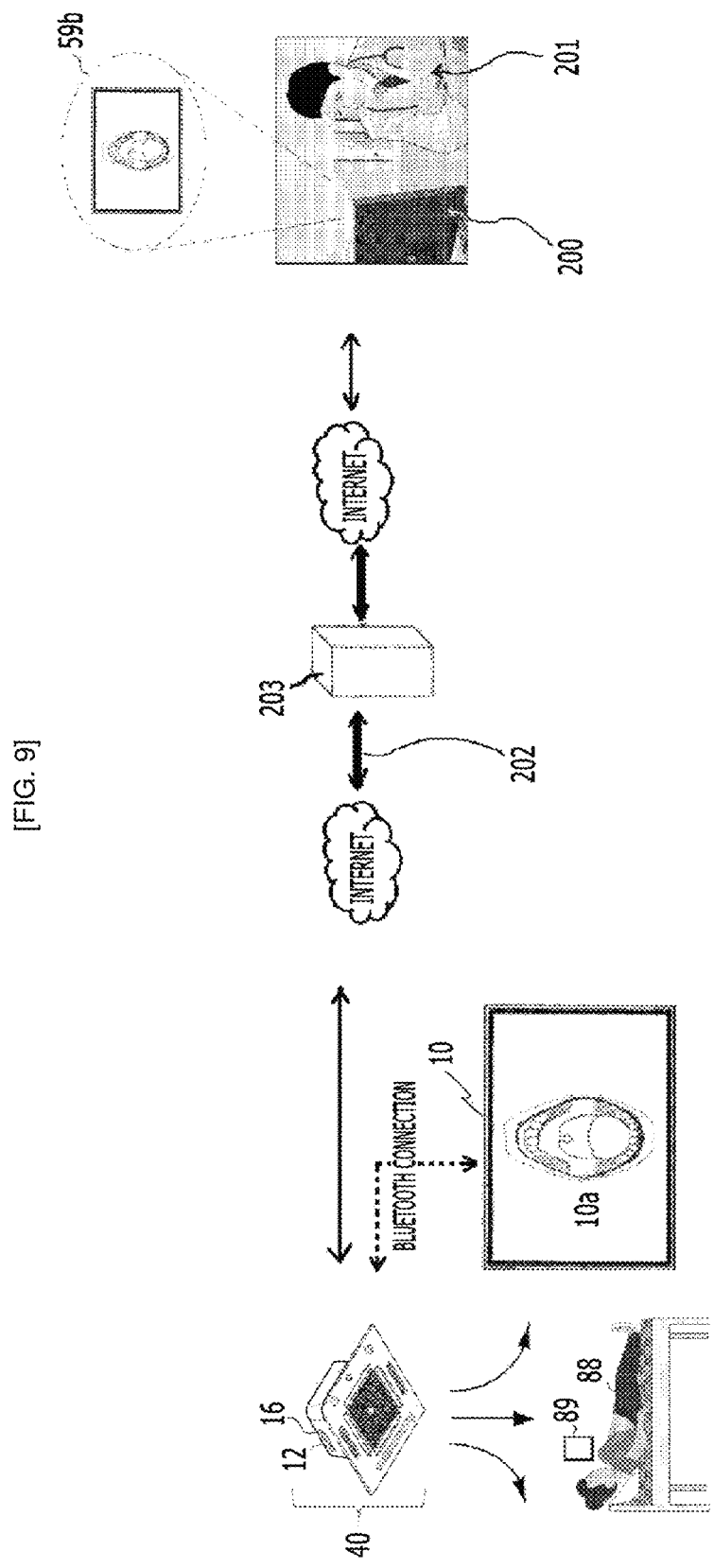

CEILING AI HEALTH MONITORING APPARATUS AND REMOTE MEDICAL-DIAGNOSIS METHOD USING THE SAME

CROSS-REFERENCE TO RELATED APPLICATIONS

This application claims the benefit under 35 USC 119(a) of Korean Patent Application No. 10-2020-0055019 filed on May 8, 2020, in the Korean Intellectual Property Office, the entire disclosure of which is incorporated herein by reference for all purposes.

BACKGROUND

1. Field

The present disclosure relates to a ceiling ai health monitoring apparatus and remote medical-diagnosis method using the same.

2. Description of the Related Art

Recently, as many people receive abundant medical benefits due to the recent increase in hospital infrastructures along with cutting-edge medical equipment technology, humanity has been promoting more happiness than in the past by extending lifespan and improving quality of life.

However, modern people who are busy in daily life cannot go to hospitals often to be put in the blind spot of medical care, and when a pandemic emerges, it is difficult to prevent the spread of the disease with the existing hospital infrastructure and medical services due to the development of transportation.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a ceiling artificial intelligence (AI) health monitoring system, includes a monitoring device provided on a ceiling of a space to acquire health information from a patient, and a medical management device configured to apply the health information of the patient acquired to an artificial intelligence-based learning model to determine health condition information of the patient and provide the determination result to a doctor monitor. The medical management device is configured to provide remote medical diagnosis information from the doctor monitor to a user terminal.

The monitoring device may include a thermographic image acquirer configured to acquire body image information of the patient using a thermal imaging camera, a microphone configured to acquire voice data including a coughing sound and a breathing sound of the patient, a speaker configured to output the remote medical diagnosis information as speech, and a digital communication module configured to provide the body image information and the voice data to the medical management device.

The medical management device may include a learner configured to apply a plurality of learning medical data to an artificial intelligence model to build a learning model, and a determiner configured to determine the health condition information by applying the health information to the artificial intelligence-based learning model. The health condition information may include information of whether the patient has a disease and a risk of the disease.

The determiner may include a breathing state determiner configured to determine a breathing state of the patient by applying the voice data to a breathing sound learning model, and a coughing state determiner configured to determine a coughing state of the patient by applying the voice data to a coughing sound learning model. The learner may be further configured to build a breathing sound learning model with a breathing database including a plurality of breathing sounds, among a plurality of learning medical data, as an input of the artificial intelligence model, and build a coughing sound learning model with a coughing database including a plurality of coughing sounds, among the plurality of learning medical data, as the input of the artificial intelligence model.

The learner may be further configured to build a coughing image learning model with thermographic medical data including a temperature distribution and a temperature value of a facial portion of the patient among the plurality of medical data for learning as the input of the artificial intelligence model, and the coughing state determiner may be further configured to apply a plurality of thermographic images representing an air temperature change in the vicinity of a mouth and a nose acquired from the thermal imaging camera to the coughing image learning model to determine whether the patient coughs.

The medical management device may further include a predicter configured to predict a risk of viral infection based on the breathing state or the coughing state of the patient which is a learning result of the breathing sound learning model and the coughing sound learning model and information indicating whether the patient coughs which is a learning result of the coughing image learning model.

The breathing state determiner may be further configured to determine sleeping state information of the patient based on a breathing state information determined based on the breathing sound learning model and the sleeping state information including sleep apnea and dyspnea.

The breathing state determiner may include a subtracter configured to obtain a per-pixel difference image between a plurality of thermographic images in the vicinity of a mouth and a nose acquired by the thermographic image acquirer with a predetermined time interval, a breathing energy calculator configured to calculate a breathing energy by a sum of squares of absolute values of all pixels of the per-pixel difference image, and a breathing determiner configured to determine a presence of breath when the breathing energy is equal to or higher than a predetermined reference value.

The medical management device may further include a subtracter configured to calculate a per-pixel difference image between a plurality of thermographic images of a breast portion acquired by the thermographic image acquirer with a predetermined time interval, a breast displacement energy calculator configured to calculate a breast displacement energy by a sum of squares of absolute values of all pixels of the per-pixel difference image, a breast displacement graph generator configured to generate a breast displacement progress graph image representing a progress and a change of the breast displacement energy over time, and a breast cancer diagnoser configured to determine whether the patient has a breast cancer using an artificial intelligence neural network built with a plurality of breast displacement progress graph images marked with a breast cancer patient or a normal patient as an input.

The medical management device may further include a sleep sensor configured to determine the patient is sleeping when an accumulated value of a sound energy included in the health information of the patient is equal to or lower than a predetermined reference value or an accumulated value of a motion changing energy of the patient is equal to or lower than a predetermined reference value.

Other features and aspects will be apparent from the following detailed description, the drawings, and the claims.

BRIEF DESCRIPTION OF THE DRAWINGS

FIG. 1 is an example in which a ceiling AI health monitoring apparatus is integrated with the main body of an air conditioner.

FIG. 2 is a view schematically illustrating a configuration of a body map mapper, an artificial intelligence network, a medical data receiver, a digital communication module, an odor and air quality analyzer, and a controller.

FIG. 3 is a view schematically illustrating an example a shape that a ceiling AI health monitoring apparatus is included in a lighting device main body.

FIG. 4A is an example in which a ceiling AI health monitoring apparatus is integrated with the main body of an air conditioner with an attached lighting device.

FIG. 4B is an example that a plastic case is installed as a separate set-top box type instead of concealing inside the main body.

FIG. 5 is a view schematically illustrating an example a body map on which body parts of interest are mapped on a body image obtained by an image sensor or a thermal imaging camera based on medical placement correlation of internal organs of a human body.

FIG. 6A is an example that determines a risk level of disease infection in accordance with a degree of fever of a thermographic image of a facial portion obtained by a body map mapper from a thermographic image of a patient by an artificial intelligence neural network which is trained in advance, as an example of a body temperature recognizer.

FIG. 6B is an example that determines breathing by an artificial intelligence neural network which recognizes a temperature change in the vicinity of a mouth and a nose between two thermographic images with a time difference obtained by a body map mapper, from thermographic video images, as an example of a breathing image recognizer.

FIG. 6C is an example that determines a risk level of breast cancer by an artificial intelligence neural network from a thermographic image of breast portions obtained by a body map mapper.

FIG. 7 is a view schematically illustrating a body map on which virtual organs of interest are mapped on a body image obtained by a 3D camera based on a medical placement correlation of internal organs of a human body.

FIGS. 8A to 8C are views schematically illustrating a 1D to 2D converter which converts a one-dimensional sound signal configured by voice command, a coughing sound, or a breathing sound input from a microphone into a two-dimensional image.

FIG. 9 is a view schematically illustrating a remote medical diagnosis method that tests sore throat by utilizing a ceiling AI health monitoring apparatus.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after understanding of the disclosure of this application may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Spatially relative terms such as "above," "upper," "below," and "lower" may be used herein for ease of description to describe one element's relationship to another element as shown in the figures. Such spatially relative terms are intended to encompass different orientations of the device in use or operation in addition to the orientation depicted in the figures. For example, if the device in the figures is turned over, an element described as being "above" or "upper" relative to another element will then be "below" or "lower" relative to the other element. Thus, the term "above" encompasses both the above and below orientations depending on the spatial orientation of the device. The device may also be oriented in other ways (for example, rotated 90 degrees or at other orientations), and the spatially relative terms used herein are to be interpreted accordingly.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

The features of the examples described herein may be combined in various ways as will be apparent after an understanding of the disclosure of this application. Further, although the examples described herein have a variety of configurations, other configurations are possible as will be apparent after an understanding of the disclosure of this application.

The present disclosure is to continuously check and manage a health condition of a patient by utilizing a health monitoring apparatus installed on a ceiling with the aid of an artificial intelligence without having the help of doctors and provide a remote diagnosis of medical specialists when a health problem occurs, and provides a ceiling AI health monitoring apparatus and method to quickly establish an infectious disease management system for suspected patients with diseases, including self-quaranitners, and efficiently manage the patients by transferring a right of control of the health monitoring apparatus to the national authorities or medical authorities in an emergency situation, such as an infectious disease.

The patient in the present disclosure may be used interchangeably with a home resident or a person who performs self-diagnosis.

In the present disclosure, a probe may commonly refer to a sensor that senses a biosignal or acquires radiology images.

In order to solve the above-described problems of the related art, an object of the present disclosure is to provide a ceiling AI health monitoring apparatus and a remote medical diagnosis method using the same, which provide guidelines for health management by collecting and judging information regarding a condition of a patient located below a ceiling of a home, such as a body temperature, a heart pulse rate, the number of coughs, and sleep apnea using a sensor and the like, with the aid of artificial intelligence, and transmitting the information to the patient by means of a feedback control commander or provide remote diagnosis or recommendation to visit hospitals through communication connection with medical specialists when health issues of the patient occur, by collecting medical data from medical equipment which is used by the patent at home by means of the wired/wireless communication and allowing the artificial intelligence to analyze the (collected) medical data.

Specifically, during emergency situations such as in the event of infectious disease, the right to control the health monitoring apparatus can be transferred to the national authorities and medical authorities to quickly establish an infectious disease management system with a cooperative system of the medical specialists and artificial intelligence to allow the authorities to directly manage the health of self-quaranitners and citizens in real-time with ceiling AI health monitoring apparatus and a remote medical diagnosis method.

By doing so, the family home itself serves as a hospital room not only to prevent the shortage of hospital rooms in the event of an infectious disease but also to minimize the direct contact of the patient with the medical personnel to prevent the infection.

According to the present disclosure, when the health monitoring apparatus is equipped on the ceiling, the state during the sleeping is observed to very optimally monitor the health of the patient at all times so that the apparatus of the present disclosure has a structure that is incorporated (included) in a ceiling type air conditioner or a ceiling type lighting device so as not to occupy a separate physical space.

However, objects to be achieved by various embodiments of the present disclosure are not limited to the technical objects as described above, and other technical objects may be present.

The present disclosure is conceived to solve the problems of the related art and a ceiling AI health monitoring apparatus of the present disclosure includes a thermal imaging camera which provides an image in which an image sensor image is overlaid on a thermal image to recognize a facial portion of a patient by a body temperature of the patient or capture a body image in real time, an lighting device installed on a ceiling wall or a ceiling type air conditioner which provides an air cleaner function and/or a cooling/heating function, an image sensor which recognizes a facial portion of the patient or captures a body image in real time, a body map mapper which obtains a body map in which body parts of interest are disposed on the body image, a microphone which receives a voice command of the patient or listens to (collects) a coughing sound or a breathing sound, a thermal imaging camera which measures a body temperature of the patient, a digital communication module which provides Internet, Bluetooth, and WiFi communication connections to allow remote medical diagnosis between the patient and a medical specialist by means of a screen displayer of the patient and a doctor monitor of the medical specialist, a screen displayer of the patient and a doctor monitor of the medical specialist which allows the sharing the screen between the patient and the medical specialist during the remote medical diagnosis, a medical data receiver which receives posture information of medical equipment or medical data information measured from the patient by the medical equipment with or without wire, an artificial intelligence neural network module which includes an artificial intelligence network deep-learned in advance using a plurality of medical data for learning, and a speaker which provides a guideline for health management, a remote medical diagnosis method, and guideline indicating how to use the medical equipment to the patient, a ceiling type main body of a lighting device or an air conditioner installed on a ceiling wall to accommodate the thermal imaging camera, the body map mapper, the microphone, the digital communication module, the medical data receiver, the artificial intelligence neural network module, and the speaker, a main body cover panel which is provided on a lower surface of the ceiling type main body and is fastened with the ceiling type main body, and a controller which applies medical data of the patient collected from the microphone, the medical equipment, and the thermal imaging camera to the deep-learning trained artificial neural network to determine whether the patient has a disease and a risk of disease and controls the input/output driving of the speaker, the screen displayer, and the digital communication module to provide the guideline for health management, a remote medical diagnosis method, and guideline indicating how to use the medical equipment to the patient based on the determination result. Further, whether the patient has a disease or the risk of disease is automatically determined by applying (using)

the deep learning trained artificial neural network using (with) medical health data of the patient collected from the microphone, the medical equipment, or the thermal imaging camera.

The image sensor preferably uses a 3D camera (three-dimensional camera) which three-dimensionally observes a body posture and a position of the patient located in an area below the ceiling and reproduces the body image of the patient in real-time and in this case, it has the advantage of specifying the position of the body parts of interest on the body image of the patient obtained from the 3D camera.

In an example, as another aspect of the image sensor or the thermal imaging camera, the image sensor or the thermal imaging camera is buried on a wall surface which forms a right angle with a ceiling wall on which the ceiling AI health monitoring apparatus is installed to be connected to the ceiling AI health monitoring apparatus. In this case, the patient may be observed not only from the ceiling, but also from the front side of the patient so that it has the benefit of recognizing a gesture, a face, a coughing image, and a body temperature.

Further, as another aspect of the image sensor or the thermal imaging camera, the image sensor or the thermal imaging camera is disposed above the screen displayer to be connected to the ceiling AI health monitoring apparatus.

The medical equipment of the present disclosure is a device including a wired/wireless transmitter which transmits medical data information measured from a sample or a diseased area of the patient to the medical data receiver through with or without a wire and may include at least one of an ultrasound scanner, a heart pulse sensor, a stethoscope, a thermometer, a urine tester, a stool tester installed in the toilet, a breast cancer diagnosis device, a blood pressure gauge, a diabetes meter, a scale, a body fat analyzer, a mobile phone camera for capturing a photograph around the tonsils and uvula in the mouth to check sore throat, a mobile phone camera for capturing a photograph of teeth in the mouth for dental examination, a portable device to file up questionnaires for health status, an eyeball (eye) examination measuring device, an automated blood analyzer, a DNA amplification test device, a virus diagnosis kit using a specific antigen of a virus, a rapid test device, a wearable device, and a cancer diagnosis device.

The virus diagnosis kit prefers an immunoassay method that utilizes characteristic reaction between antigen and antibody to sensitively screen virus, a form of antigen, from antibody coated with gold nanoparticles.

The rapid test device preferably includes a capture probe on a porous membrane.

The wearable device may include a device on which biosensors performing a health care function are attached, such as a watch, glasses, and smart clothing.

As for the blood pressure gauge and a heart pulse sensor, a sensor attached to a smartwatch, which is worn on a wrist, is preferable, and medical data measured from the wrist is transmitted to the medical data receiver, preferably by Bluetooth communication.

The stool tester installed in the toilet is preferably provided with a sensor around the toilet drain to perform a fecal occult blood test in the toilet to inform the risk of colon cancer and rectal cancer in which cancer cells occur from the epithelial cells of the colon.

The eyeball examination measuring device is preferably a device that captures an image of the eye to examine cataracts, glaucoma, jaundice, and yellowness and preferably observes the patient's eyes, including the cornea, iris, and pupil, using a camera on the mobile phone while looking at the mobile phone screen to transmit corresponding images to the medical data receiver of the ceiling AI health monitoring apparatus to constantly test and check the patient before the patient is aware.

In this case, the ceiling AI health monitoring apparatus preferably informs the risk of cataracts, glaucoma, jaundice, and yellowness of the patient by allowing the artificial intelligence neural network to analyze and observe the change in response of the cornea, iris, and pupil in accordance with brightness, font size, color type, and sharpness of various mobile phone screens represented on the mobile phone screen over a long term.

The DNA amplification test device is preferably a LAP on a chip or a rotatable Lab on a disc to diagnose and detect a small amount of material in a fluid by polymer chain reaction (PCR) and preferably performs a virus test by extracting RNA from a sample taken with a swab from blood, urine, salvia, oral cavity, and anus and amplifying a complementary DNA (cDNA).

The automated blood analyzer and the cancer diagnosis device are preferably rotatable Lab on a disc and desirably determine cancer from a blood sample.

The Lab on a Disc is preferably configured by a sample inlet port through which a sample is injected, a sample chamber that stores the sample injected through the sample inlet port, an analyte chamber, and a remnant chamber that separates a sample of the sample chamber by centrifugation into a quantitative analyte and remnant to separately store them, an extra chamber which stores an excess sample of the analyte chamber to store the quantitative analyte in the analyte chamber, one or more analysis sites in which a capture probe for specific binding with a material in the analyte is fixed and/or a reagent for biochemical reaction with the analyte is stored, a trash chamber which collects debris which is not bound to the capture probe by a cleaning process, a channel which connects the chambers, and a valve which controls the flow and a movement of liquid between the chambers.

Desirably, as another aspect of the analysis site of the Lab on a Disc or the rapid test device, various types of tumor markers or disease markers are fixed on a porous membrane as a test line or a spot, and the porous membrane may have a strip shape which entirely allows lateral flow or flow-through of the fluid. The porous membrane may include a sample pad and a conjugate pad on one terminal and an absorbent pad on the other terminal. The tumor marker or the disease marker may be AFP, PSA, CEA, CA19-9, CA125, CA15-3, a marker of Alzheimer's disease, or a marker of myocardial infarction.

The mobile phone camera for checking sore throat or examining teeth preferably captures a photograph around the tonsils and uvula in the mouth to transmit the photograph to the medical data receiver of the ceiling AI health monitoring apparatus. The artificial intelligence neural network of the ceiling AI health monitoring apparatus analyzes the images to determine the status of the sore throat and the risk of the dental health of the patient to inform the patient.

The portable device for filing the questionnaire asking the health condition preferably generates medical information of the patient such as an experience of visiting an overseas disease risk area within the last one month, difficulty breathing, sore throat, cough, high fever, or muscle pain using a graphic user interface (GUI) and sends the information to the medical data receiver.

Another aspect of the present disclosure further includes an odor sensor in an air inlet port of the ceiling type air conditioner to collect the odor of the patient.

Further, the odor is collected by the air inlet port so that the odor discharged when the patient breaths may be effectively checked even at a distance far from the patient.

The odor sensor preferably analyzes a concentration of various volatile organic compounds included in a breathing gas of the human during the sleeping, for example, a concentration of toluene to diagnose the risk of lung cancer or analyze a concentration of acetone gas to diagnose a risk of diabetes.

Generally, normal people discharge 900 parts per billion (ppb) of acetone gas, but diabetic patients exhale 1800 ppb of acetone gas. When the odor sensor precisely analyzes the concentration difference of the acetone gas during the breathing, diabetes may be diagnosed at an early stage.

Another aspect of the present disclosure further includes an ultraviolet (UV) LED, a UV lamp, or a plasma heater in the air inlet port of the ceiling type air conditioner to sterilize viruses or bacteria contained in the introduced air and release them to the ejecting port.

The plasma heater instantly kills the viruses and bacteria by plasma heating while the UV LED removes the bacteria by the LED, which emits ultraviolet rays.

The posture information of the medical equipment is preferably any one selected from a position of the probe of the medical equipment on the body, a contact pressure of the probe on a diseased area, contact inclination information of the probe on the diseased area.

For example, when the medical equipment is an ultrasound scanner, the patient measures an ultrasound image from the diseased area by the contact between the diseased area and the ultrasound probe and the posture information of the ultrasound scanner may be information including a current position coordinate of the ultrasound scanner on the body of the patient, a contact pressure indicating how strong the ultrasound probe is pressurized on a skin surface around the diseased area to scan and a contact inclination (incident angle) of the ultrasound probe with respect to the diseased area.

The guideline about how to use the medical equipment includes a posture correction necessary to use the medical equipment.

For example, it is preferable to include a voice command including a correction of an inclination (incident angle) of the ultrasound probe, a pressure correction, and a position correction required to maintain an ultrasound scanner posture optimized for diagnosis item and the diagnosis site based on the posture information of the ultrasound scanner and a voice message for guidance and instructions for ultrasound diagnosis.

The medical equipment data analyzer of the present disclosure preferably uses an artificial intelligence neural network trained by medical data labeled for every disease type and risk level for test items performed by the medical equipment.

Desirably, in the present disclosure, the coughing sound recognizer preferably uses an artificial intelligence neural network for recognizing a coughing sound, which is trained in advance using a coughing sound database for learning configured by various coughing sounds input from the microphone.

Desirably, in the present disclosure, the coughing image recognizer preferably uses an artificial intelligence neural network for recognizing a coughing image, which is trained in advance using a coughing image database for learning configured by two thermographic coughing images with a time difference showing a temperature change in the air in the vicinity of the mouth and the nose acquired from the thermal imaging camera when coughing occurs.

Desirably, the coughing sound recognizer and the coughing image recognizer of the present disclosure determine whether there is coughing, and the controller cumulatively manages the number of coughing to measure the frequency of the coughing.

Desirably, in the present disclosure, the breathing sound recognizer preferably uses an artificial intelligence neural network for recognizing a breathing sound, which is trained in advance using a breathing sound database for learning configured by various breathing sounds input from the microphone.

Desirably, in the present disclosure, the breathing image recognizer preferably uses an artificial intelligence neural network for recognizing a breathing image, which is trained in advance using a breathing image database for learning configured by various thermographic breathing images which recognize a temperature change in the vicinity of the mouth and the nose input from the thermal imaging camera.

Desirably, the breathing sound recognizer and the breathing image recognizer of the present disclosure determine whether there is breathing, and the controller accumulatively manages the number of breathings to measure the frequency of the breathing to determine sleep apnea or check dyspnea, or predict the heart pulse rate.

Desirably, when the controller determines the sleep apnea or determines that the dyspnea occurs, the controller preferably reports the condition of the patient by automatically making a call (auto dialing) to a predetermined emergency contact number or an emergency room such as 119 or 911 by means of the digital communication module. The emergency contact number may be a contact number of acquaintances or relatives, and the controller further includes a memory to store the emergency contact numbers through an application installed in the mobile phone using a Bluetooth connection.

Desirably, the voice command recognizer of the present disclosure preferably uses an artificial intelligence neural network for voice command recognition, which is trained in advance using a voice database for learning configured by various voice samples input from the microphone and preferably recognizes a voice command of the patient by the artificial intelligence neural network for voice command recognition or measures patient's sore throat, vocal cord health condition, and risk of senile disorder.

Desirably, the voice command is preferably a voice instruction of the patient to control a function of the screen displayer or a voice question of the patient to listen to information provided by the screen displayer. For example, a voice command, such as "Turn on TV" or "Turn off TV," or a voice question such as "What time is it now?" may be included.

Desirably, another aspect of the measurement of patient's sore throat, vocal cord health condition, and risk of senile disorder measures whether there is a frequency component having elements of patient's sore throat, vocal cord health condition, and risk of senile disorder by analyzing a voice of the voice command of the patient in a frequency domain.

Desirably, the voice database for learning, which trains the artificial intelligence neural network for voice command recognition, preferably uses a disease voice database in which a voice collected for every disease is labeled with the name of a disease.

For example, the disease voice database may label the voice instruction or voice questions obtained from the patient with a sore throat to store therein and store a voice instruction or a voice question of a person who does not have a disease by labeling with "no sore throat" in the disease voice database. Thereafter, when there is a patient's voice command, the artificial intelligence neural network for voice command recognition may determine whether the patient has a sore throat.

The voice database for learning configured by various voice samples input from the microphone is generated (obtained) as a disease voice database in which a voice collected for every disease is labeled with a name of the disease.

Desirably, the database for learning configured by the voice command, the coughing sound, or the breathing sound input from the microphone preferably trains the artificial intelligence neural network by converting it into a two-dimensional image by a "1 D to 2D converter".

Accordingly, the voice command, the coughing sound, or the breathing sound input from the microphone after training the artificial intelligence neural network is converted into a two-dimensional image by the "1D to 2D converter" to be input to the artificial intelligence neural network.

In the present disclosure, the face recognizer preferably recognizes the face of the patient using an artificial intelligence neural network for face recognition trained with a face image of the patient used when the patient is registered in the ceiling AI health monitoring apparatus of the present disclosure using a face image database for learning.

In this case, when a plurality of people lives in a house, personal identification is possible by the face recognizer, which enables individual health monitoring.

Desirably, as the face image database for learning, a patient face image obtained from the mobile phone camera, an image sensor, or a thermal imaging camera is preferable.

The thermal imaging camera, which recognizes a facial portion of the patient by the body temperature of the patient or captures a body image in real-time, is not only advantageous to recognize the face of the patient in the dark or in sleep, but also advantageous for various environments because it is less affected by the illumination.

The body map of the present disclosure refers to a placement chart in which body parts of interest are specified to be disposed on the body image by a body map mapper.

Desirably, the body map mapper of the present disclosure preferably uses an artificial intelligence neural network which is trained in advance by body images, which are semantic segmentation labeled in the unit of pixels using different colors for body parts of interest and then obtains a semantic segmented image for every pixel labeled with different colors for each body part of interest by performing semantic segmentation on the body image of the patient given from the image sensor and thus specifies the position and the area of the body part of interest on the body image.

Desirably, another aspect of the body map mapper which specifies a position of the body parts of interest on the image of the patient obtained from the thermal imaging camera uses an artificial intelligence neural network which is trained in advance by thermographic images, which are semantic segmentation labeled for body parts of interest and then obtains a semantic segmented image for every pixel labeled with different colors for each body part of interest by performing semantic segmentation on the body image of the patient given from the thermal imaging camera. By doing this, the position and the area of the body part of interest may be identified.

The body part of interest of the present disclosure is preferably a face, a forehead, and any one or more body parts selected from human body parts requested for the test of the medical equipment.

The artificial intelligence neural network of the present disclosure preferably uses a Convolutional Neural Network (CNN) or a Recurrent Neural Network (RNN), but is not limited thereto.

In the present disclosure, the artificial intelligence neural network is a neural network that allows deep learning and is combined and configured by one or more layers or elements selected from a convolution layer, a Pooling layer, a ReLu layer, a Transpose convolution layer, an unpooling layer, a 1×1 convolution layer, skip connection, a global average pooling (GAP) layer, a fully connected layer, a support vector machine (SVM), a long shout term memory (LSTM), atrous convolution, atrous spatial pyramid pooling, separable convolution, and bilinear upsampling. The artificial intelligence neural network preferably further includes an operating unit for batch normalization operation at a front end of the ReLu layer.

The semantic segmentation of the present disclosure is an artificial intelligence neural network which, when there is a body part of interest in the given body image, classifies the body parts of interest in the unit of pixels to determine which position is included and divides them from other objects and is preferably trained in advance by a body part image database labeled with different colors (color labeled) for each body part of interest.

The body part image database is preferably configured by the body parts of a normal person who does not have a disease in the vicinity of the body part of interest.

Desirably, another aspect of the body map mapper of the present disclosure is implemented by a body map in which body parts of interest are mapped on a body image obtained by the image sensor or the thermal imaging camera based on a medical placement correlation of organs of a human body.

The body map is preferably an image obtained by labeling major body parts of interest, such as a face (head), an arm, or a leg with different colors on the body image, and the body parts of interest may be marked on the body image obtained from the image sensor or the thermal imaging camera in accordance with a physical placement situation between internal organs of a human body.

To this end, it is preferable to find the head, trunk, arm, and leg parts, including an outline of the body from the body image first, and specify and dispose another body part of interest such as a nose, a mouth, a neck, or a finger on the body image with the head, trunk, arm and leg parts as a body reference point.

The thermal imaging camera of the present disclosure is a device that generates a thermographic image and is preferably a device that detects heat radiation emitted from the body using infrared ray, visualizes the heat radiation with various colors according to the temperature of the body surface to show it as an image, and tracks and detects the heat to show the heat on the screen at a glance.

Another object of the thermographic image of the present disclosure overlays an image of a normal camera, for example, an image sensor, on the thermographic image, and in this case, it is very advantageous to improve the performance of the body map mapper because an outline boundary and details of the body are more clearly distinguished on the body image to specify and dispose the body parts of interest on the body image.

Desirably, as a body part of interest of the present disclosure, any one or more body parts selected from a face, a lip, a nose, a forehead, a neck, a chest, eyes, and eyebrows are preferable.

The patient registration of the ceiling AI health monitoring apparatus of the present disclosure is preferably performed by a home page on the Internet or a mobile device and preferably performed by inputting patient information including gender (sex), age, height, weight, a waist size, an underlying disease list, and disease history of the input patient.

The patient identification of the ceiling AI health monitoring apparatus of the present disclosure is preferably performed by any one method selected from face recognition registered at the time of patient registration, fingerprint recognition, iris recognition, voice recognition, ID identification, and identification through a mobile device.

The body temperature measurement of the present disclosure is preferably obtained by an average or a maximum value of pixel data values on a thermographic image of any one part selected from a head part, a facial portion, an eye part, and a neck part on the body image obtained by the body map mapper.

The 3D camera of the present disclosure provides depth information as well as two-dimensional image information for a patient's body and is preferably configured by an infrared (IR) laser projector which projects and radiates structured light configured by tens of thousands of specific patterns (straight lines, dot pattern, or lattice pattern) onto a patient's body, an IR camera which analyzes a deformed degree of the radiated laser pattern according to a shape of the body surface of the patient to measure a depth, and a 3D operating device which calculates the measured depth and then composes a two-dimensional body image captured by the image sensor to derive a three-dimensional body image.

The sleep sensor of the present disclosure is to determine whether the patient sleeps and desirably determines whether the patient sleeps using artificial intelligence, which is trained in advance by various thermographic body images of the patient in sleep.

The above-described solving means are merely illustrative but should not be construed as limiting the present disclosure. In addition to the above-described embodiments, additional embodiments may be further provided in the drawings and the detailed description of the present disclosure.

According to the aspect of the present disclosure, it is possible to continuously check and manage a health condition of a patient by utilizing a health monitoring apparatus installed on a ceiling with the aid of artificial intelligence without having the help of doctors and provide a remote diagnosis of medical specialists when a health problem occurs, and to quickly establish an infectious disease management system for suspected patients with diseases, including self-quarantiners, and efficiently manage the patients by transferring a right of control of the health monitoring device to national authorities or medical authorities in an emergency situation, such as an infectious disease.

FIG. 1 is an example in which a ceiling AI health monitoring apparatus 40 is integrated with an air conditioner main body 1a, FIG. 3 is an example in which a ceiling AI health monitoring apparatus 40 is integrated with a lighting device main body 1b, and FIG. 4 is an example in which a ceiling AI health monitoring apparatus 40 is integrated with an air conditioner main body 1c with an attached lighting device.

Hereinafter, a ceiling type main body refers to any one of a ceiling type air conditioner main body 1a, a lighting device main body 1b, and an air conditioner main body 1c with an attached lighting device.

FIGS. 1, 4A, and 4B illustrate an example in which a ceiling AI health monitoring apparatus 40 is integrated with main bodies 1a, 1b, and 1c installed on the ceiling. In an example, the ceiling type main body 1a, 1b, and 1c buried on a ceiling wall may include a thermal imaging camera 22, a body map mapper 4, a microphone 6, a digital communication module 8, a screen displayer 10, a data receiver 12, an artificial intelligence neural network module 16, a speaker 2, main body cover panels 2a, 2b, 2d. and a controller 60.

In an example, the thermal imaging camera 22 observes a patient 88 located below the ceiling type main bodies 1a, 1b, 1c and reproduces a body image of the patient in real-time or recognizes a face portion of the patient by a body temperature of the patient 88 or measures a body temperature of the patient. Further, the body map mapper 4 may acquire a body map in which a plurality of body parts of interest is specified on the body image. The microphone 6 may receive a voice command of the patient or acquire breathing sounds.

The digital communication module 8 may provide Internet and WiFi connection, which allow remote medical diagnosis by means of a mobile phone of the patient and a doctor monitor of a medical specialist. Further, the digital communication module 8 may provide Internet and WiFi connection which allow remote medical diagnosis between the patient and the medical specialist by means of the screen displayer 10 of the patient and a doctor monitor 20 of the medical specialist.

Further, the screen displayer 10 may share screens between the patient and the medical specialist during the remote medical diagnosis. The screen displayer 10 preferably uses television or a screen of a mobile phone.

The data receiver 12 may receive posture information of the medical equipment 69 or medical data information measured by the medical equipment 69 by using wired and wireless.

Further, the artificial intelligence neural network module 16 may include an artificial neural network, which is deep-learning trained in advance using a plurality of medical data for learning.

Further, the speaker 17 may transmit a feedback control command to the patient to provide a guideline for health management, a remote medical diagnosis method, and a guideline about how to use the medical equipment 69.

In the meantime, the main body cover panels 2a, 2b, and 2d may be fastened with the ceiling type main body 1a, 1b, and 1c so that lower surfaces of the ceiling type main bodies 1a, 1b, and 1c are not seen from the outside.

Further, the ceiling AI health monitoring apparatus 40 may include the controller 60, which applies the medical data of the patient acquired from the microphone 6, the medical equipment 69, and the thermal imaging camera 22 to the deep-learning trained artificial intelligence neural network module 16 to automatically determine whether the patient has a disease or a risk of the disease and controls the input/output operation of the speaker 17, the screen displayer 10, and the digital communication module 8 according to the determination result.

According to an example of the present disclosure, the ceiling AI health monitoring apparatus 40 further includes an image sensor 20 to observe a body posture and a position of the patient and reproduce a body image of the patient according thereto in real-time and further includes a gesture recognizer (denoted by reference numeral 16g in FIG. 2) which recognizes a gesture command of the patient in real-time to control the screen displayer 10 to be turned on/off, channel up/down, and volume up/down.

According to an example of the present disclosure, the gesture recognizer 16g preferably includes an artificial intelligence neural network that recognizes a gesture image of the patient from the thermal imaging camera 22 or the image sensor 20.

The gesture recognizer 16g preferably recognizes three-dimensionally a gesture command such as a finger, a grasped shape of fingers, or a hand gesture of the patient, specifies a position of the finger and the arm by the body map mapper 4, and preferably recognizes the gesture command of the patient from the thermographic video image using an artificial intelligence neural network which recognizes the gesture command of the patient by the finger and arm motion.

A plurality of thermal imaging cameras 22 and a plurality of image sensors 20 may be provided to recognize a three-dimensional gesture.

A clock displayer 85 may be provided on the main body cover panels 2a, 2b, and 2d. The clock displayer 85 displays a current time by the gesture command or the voice command and is automatically turned off within two to five seconds.

The screen displayer 10 may provide visual education and user's guide information about how to use medical equipment during remote medical diagnosis.

The imaging sensor 20 and the thermal image camera 22 are preferably attached to the main body cover panels 2a, 2b, and 2d above a bed 19 where the patient 88 lies to perform self-diagnosis so as to properly observe the patient 88, and in this case, it is advantageous to design a sleep sensor 18 to check whether the patient sleeps. The sleep sensor 18 of the present disclosure is provided to determine whether the patient is sleeping and may determine whether the patient sleeps using artificial intelligence, which is trained in advance by various thermographic body images of the patient on the bad which is marked with non-sleep and sleep. Further, when an accumulated value of sound energy is equal to or lower than a predetermined reference value or an accumulated value of a motion changing energy of the patient is equal to or lower than a predetermined reference value, for a predetermined time, for example, for five minutes, the controller 60 may determine that the patient is sleeping.

Various thermographic body images of the patient on the bed marked with non-sleep and sleep are preferably specified by eyes, which are a body part that can easily be identified whether the patient is closing or opening the eyes.

Desirably, the sleep sensor 18 using sound energy calculates the sound energy by a sum of squares of absolute values of sound pixels obtained for each predetermined time interval, accumulatively calculates the sound energy for a predetermined time, and compares the accumulated value with a predetermined value to determine whether the user sleeps.

Desirably, the sleep sensor 18, using the motion changing energy of the patient, obtains a difference image for each pixel between two thermographic images obtained by capturing the bed with a time interval t, calculates the motion changing energy of the patient by a sum of squares of absolute values of all pixels in the difference images, accumulatively calculates the motion changing energy for a predetermined time, and compares the accumulated value with a predetermined reference value to determine whether the user sleeps.

The body map mapper 4, the artificial intelligence neural network module 16, the digital communication module 8, the medical data receiver 12, the odor and air quality analyzer 67, and the controller 60 are accommodated in a plastic case 100 in the ceiling type main bodies 1a, 1b, and 1c to be concealed, buried, and assembled to be fixedly installed. Further, the image sensor 20, the speaker 17, the microphone 6, and the thermal imaging camera 22 are buried in accommodating spaces 30a, 30b, 30c, 30d, 30e, and 30f provided on the ceiling type main body 1a, 1b, and 1c and input/output parts thereof are exposed to the external surfaces through openings provided on the main body cover panels 2a, 2b, and 2d.

Referring to FIGS. 1 and 4A, air entering through the air inlet port 72 is sucked by a motor 50a fixed on an upper bottom surface in the ceiling type main body 1a and 1c and an air blower fan 50b fitted with a motor shaft of the motor 50a and is converted into cold wind or hot wind by a heat exchanger (denoted by a reference numeral 62 in FIG. 4B) to be ejected through an ejecting port 70. Preferably, an odor sensor 27 is disposed in the air inlet port 72.

In the air inlet port 72, an air filter 28 is disposed to intake dirty air to eject filtered clean air through the ejecting port 70. In this case, the odor sensor 27 preferably also serves as a sensor that evaluates the air quality.

The odor sensor 27, which evaluates the air quality, preferably evaluates the air quality with fine particulate matters, radon, and carbon dioxide concentrations in the air.

Reference numeral 77 denotes an ultraviolet (UV) LED, a UV lamp, or a plasma heater, which is provided above the air inlet port 72 to sterilize viruses or bacteria contained in the introduced air and release it to the ejecting port 70.

FIG. 2 is a view schematically illustrating a configuration of a body map mapper, an artificial intelligence network, a medical data receiver, a digital communication module, an odor and air quality analyzer, and a controller which are buried together in a plastic case together.

FIG. 2 shows components of the body map mapper 4, the artificial intelligence neural network module 16, the medical data receiver 12, the digital communication module 8, the odor and air quality analyzer 67, and the controller 60, which are accommodated and buried together in the plastic case 100 and a connection relationship there-between.

In an example, the odor and air quality analyzer 67 analyzes a concentration of toluene from the odor sensor 27 to diagnose risk of lung cancer or analyzes a concentration of acetone gas to diagnose risk of diabetes.

Another aspect of the odor and air quality analyzer 67 analyzes fine particulate matters, radon, carbon dioxide, and oxygen concentrations from the odor sensor 27 to analyze the air quality.

In an example, the artificial intelligence neural network module 16 may include the voice command recognizer 16a, the breathing sound recognizer 16b, the coughing sound recognizer 16c, a coughing image recognizer 16d, a breathing image recognizer 16e, a face recognizer 16f, the sleep sensor 18, the gesture recognizer 16g, a body temperature recognizer 16h, the body map mapper 4, and a medical equipment data analyzer 16i.

The voice command recognizer 16a may recognize voice commands of the patient from a microphone input signal input from the microphone 6. Further, the voice command recognizer 16a may recognize a voice command of the patient from the microphone input signal input from the microphone 6 using the artificial intelligence neural network, which is trained with necessary voice commands in advance by a labeling learning database.

The breathing sound recognizer 16b may determine whether the patient breaths from the microphone input signal, using the artificial intelligence neural network, which is trained in advance using a learning database configured by various breathing sounds input from the microphone 6.

The coughing sound recognizer 16c may determine whether the patient coughs from the input signal provided from the microphone 6, using the artificial intelligence neural network, which is trained in advance using a learning database configured by various coughing sounds input from the microphone 6.

The coughing image recognizer 16*d* may determine whether the patient coughs from a thermographic image, using the artificial intelligence neural network, which is trained in advance using the thermographic image database in the air in the vicinity of the mouth and the nose obtained from the thermal imaging camera 22 during the coughing.

Further, the breathing image recognizer 16*e* may determine whether the patient breaths from the thermographic image, by the artificial intelligence neural network trained in advance using the image database configured by various thermographic breathing images which show temperature changes in the vicinity of the mouth and the nose input from the thermal imaging camera 22 during the breathing.

Further, the face recognizer 16*f* may recognize the face of the patient from the thermographic image, using the artificial intelligence neural network, which is trained in advance by face images of the patient input from the thermal imaging camera 22.

The sleep sensor 18 may determine whether the patient sleeps using artificial intelligence, which is trained in advance by various body images of the patient in sleep from the thermal imaging camera 22.

Further, the gesture recognizer 16*g* may recognize a body motion command of the patient from the thermographic video image using the artificial intelligence neural network, which recognizes the gesture image of the patient input from the thermal imaging camera 22.

Further, the body temperature recognizer 16*h* may determine a risk level of disease infection in accordance with a degree of fever of the face area, by the artificial intelligence neural network which is trained in advance using an image database configured by various thermographic images which show a temperature distribution and a temperature value of the face area of the patient input from the thermal imaging camera 22.

Further, the body map mapper 4 may acquire a body map in which body parts of interest are specified to be disposed on the body image of the patient, from the thermographic image input from the thermal imaging camera 22. Further, the medical equipment data analyzer 16*i* may analyze various medical data information received from the medical equipment in use input from the medical data receiver 12.

In an example, when a plurality of patients uses the ceiling AI health monitoring apparatus, the coughing sound recognizer 16*c* or the breathing sound recognizer 16*b* may individually recognize the patients to distinguish and recognize each patient's coughing sound or each patient's breathing sound, using the artificial intelligence neural network which is trained in advance using various utterance data of patients input from the microphone 6.

Since every people has different voices, it is possible to distinguish the owner of the breathing sound and coughing sound by the artificial intelligence having an ability to extract unique feature information of an utterer included in a voice wave to automatically determine the utterer of the sound.

The thermographic image of the thermal imaging camera 22 of the present disclosure may be replaced with an image acquired from the image sensor 20 or an image in which the thermographic image is overlaid on the image sensor image.

In an example, the controller 60 may determine the health condition of the patient with analysis result data of the artificial intelligence neural network module 16. Further, the controller 60 may control the operations of the digital communication module 8, the speaker 17, and the screen displayer 10 to provide a guideline about health management, a remote medical treatment method, and a guideline about how to use medical equipment to the patient according to the determination of the patient's health condition.

The controller 60 preferably transmits a guideline about health management, a remote medical treatment method, and a guideline about how to use medical equipment as a text through a mobile device or Internet e-mail of the patient through the digital communication module 8.

The controller 60 may provide a guideline about health management through a mobile device or Internet e-mail of the patient through the digital communication module 8 according to the result of the odor and air quality analyzer 67.

The controller 60 may control the screen displayer 10 to share the screen between the patient and the medical specialists during the remote medical diagnosis.

For example, another aspect of the controller 60 may include a control right transferring means to transfer a control right of the ceiling AI health monitoring apparatus to the disease management authority in the case of a national emergency, especially in an emergency situation such as the spread of infectious diseases.

Desirably, the control right transferring means allowing the disease management authority which receives the control right of the ceiling AI health monitoring apparatus to control and use the ceiling AI health monitoring apparatus through the digital communication module 8, to directly transmit the health management guideline to the patient through the microphone 6 and the screen displayer 10, check a body temperature and a health condition of the patient through the remote diagnosis, and read recent health history information of the patient stored in the ceiling AI health monitoring apparatus.

Desirably, when the patient receives the request for transferring the control right of the ceiling AI health monitoring apparatus from the disease management authority and accepts the request transferring for the control right via a predetermined authentication procedure through a computer app, the control right transferring means allow the disease management authority to have the control right of the ceiling AI health monitoring apparatus. In this case, the disease management authority may have a control right and a usage right of the ceiling AI health monitoring apparatus by means of the digital communication module.

For example, referring to (d) of FIG. 4B, another aspect of the plastic case 100 is installing as a separate set-top box instead of being concealed in the main bodies 1*a*, 1*b*, and 1*c*.

The reference numeral 999 denotes a 1D to 2D converting means, which converts a one-dimensional sound signal configured by voice command, a coughing sound, or a breathing sound input from the microphone 6 into a two-dimensional image.

FIGS. 3A and 3B illustrate an example in which the ceiling AI health monitoring apparatus is integrated with a lighting device main body 1*b* installed on the ceiling and FIG. 3B is a cross-sectional view for a cross-section a-a' of FIG. 3A.

An LED light 120 disposed in the lighting device 2*c* is preferably configured by a plurality of LEDs 131 disposed on a metal PCB board 130 with a regular interval, a base 150 which encloses both ends and is formed of an insulating material, and a connection pin 152 which protrudes from the outer surface of the base 150 and is formed of a conductive material inserted into a socket to which electricity is supplied.

FIG. 4A(a) and (b) illustrate an example in which the ceiling AI health monitoring apparatus is integrated with an air conditioner main body 1*c* with an attached lighting device installed on the ceiling and FIG. 4A(b) is a cross-sectional view for a cross-section b-b' of FIG. 4A(a).

The air conditioner main body 1*c* with an attached lighting device may include a motor 50*a* and an air blower fan 50*b* fitted with a motor shaft of the motor 50*a* to suck air from the lower side installed in an inner center, a heat exchanger 62 to exchange sucked air into heat installed on the outside of the air blower fan 50*b*, and a condensed water receiver 64 to receive condensed water generated from the heat exchanger 62 installed below the heat exchanger 62.

On the lower surface of the air conditioner main body 1*c* with an attached lighting device, an air inlet port 72 through which air is introduced and an ejecting port 70 through which air passing through the heat exchanger 62 is ejected are simultaneously formed.

Reference numeral 66 is a connection rod that connects the main body cover panel 2*d* and the lighting device 2*c* to be spatially spaced apart from each other and allows a sufficient amount of air to be introduced into the air inlet port 72 when the air blower fan 50*b* operates.

The reference numeral 131 denotes a plurality of LEDs, which is disposed on the metal PCB board 130 with a regular interval.

Reference numeral 131*a* denotes a reflector that reflects light from the LED 131 to increase the efficiency of the illumination.

FIG. 4B(c) and (d) illustrate an example in which the plastic case 100 is installed as a separate set top box instead of being concealed in the main bodies 1*a*, 1*b*, and 1*c* and FIG. 4B(c) illustrates an example in which the plastic case 100 is modified as the shape of the speaker 17 and FIG. 4B(d) illustrates an example in which the plastic case 100 is modified as an internet router.

Further, another example of the plastic case 100 is preferably modified as a ceiling type to properly observe the patient to be buried in the ceiling wall, and the microphone 6, the speaker 17, the thermal imaging camera 22, and the image sensor 20 are exposed from the ceiling wall.

FIG. 5 illustrates an example of a body map on which body parts 90*a*, 90*b*, 90*c*, 90*d*, and 90*e* of interest are mapped on a body image 90 obtained by an image sensor 20 or a thermal imaging camera 22 based on medical placement correlation of internal organs of a human body.

The mapping task is performed on the body image 90 using a grid pattern 91 to smoothly map the body map.

To this end, first, head 90*a*, neck 90*b*, trunk 90*c*, arm 90*d*, leg 90*e*, and finger 90*f* parts including an outline of the body are found from the body image 90 and bodies of interest such as a mouth, a nose, or a forehead are identified on the body image 90 with the parts as a body reference point to identify the position and the area of the body part of interest therefrom.

In an example of the drawing, body parts of interest are labeled with different colors. For example, the head 90*a* is labeled with green, the neck 90*b* is labeled with yellow, the trunk 90*c* is labeled with gray, the leg 90*e* is leveled with pink, and the finger 90*f* is labeled with yellow green to be mapped.

FIG. 6A shows an example that determines a risk level of disease infection in accordance with a level of fever of a thermographic image 140*b* of a face area obtained by a body map mapper 4 from a thermographic image 140*a* of a patient by a previously trained artificial intelligence neural network and represents a risk level of disease infection in accordance with a hot level of the face or the forehead, as an example of a body temperature recognizer 16*h*.

Desirably, another aspect of the body temperature recognizer 16*h* of the present disclosure determines a risk level of the disease infection according to an average or a maximum value of thermographic image pixel data values of any one part selected from a head part, a facial portion, an eye part, and a neck part on the body image.

FIG. 6B shows an example which determines breathing by an artificial intelligence neural network that recognizes a temperature change in the vicinity of a mouth and a nose between two thermographic images 79*a* and 79*b* with a time difference obtained by the body map mapper 4, from thermographic video images 80*a* and 80*b* and when it is determined that the patient breaths, the controller 60 accumulatively manages and measures the frequency of the breathing to determine sleep apnea syndrome or measure a heart pulse rate, as an example of a breathing image recognizer 16*e*. For example, whether the patent sleeps may be determined by the sleep sensor 18.

Reference numeral 80*b* illustrated in FIG. 6B denotes a thermographic image obtained a time Δt later after obtaining the thermographic image denoted by reference numeral 80*a*. In the present disclosure, the time Δt may be any one frame of time interval selected between one frame and 120 frames.

Desirably, as the artificial intelligence neural network recognizes the breathing operation, an artificial intelligence neural network which is trained in advance using a database configured by various thermographic breathing images in the vicinity of the mouth and the nose, received from the thermal imaging camera is preferably used.

FIG. 6C is an example of a breast cancer diagnoser (FIG. 6C), which determines the risk level of breast cancer of the patient using an artificial intelligence neural network 71*a*, which is trained in advance by pattern images of a thermographic image of a tumor of breast portions, with the thermographic image 150*b* of the breast portion obtained by a body map mapper 4.

For example, the patient takes an orally administered imaging agent containing a contrast material that only adheres to breast cancer cells, and then, the body image of the patient may be obtained by the thermal imaging camera 22. Further, the body map mapper 4 may specify the breast portion on the body image of the patient obtained from the thermal imaging camera 22. The breast cancer diagnoser (FIG. 6C) informs a risk level of the breast cancer of the patient using the artificial neural network 71*a*, which is deep-learning trained to detect heat from the tumor of the breast portion to diagnose the breast cancer.

Desirably, another aspect of the risk level of breast cancer is obtained by an average or a maximum value of the thermographic image pixel data values of the breast portion.

Desirably, according to an example, in order to reduce an erroneous detection rate of breast cancer due to the body temperature, the risk level of breast cancer is determined from the thermographic image 150*b* of the breast portion by the artificial intelligence neural network 71*a*, after a calibration process for cooling the body of the patient for a predetermined time by the ceiling type air conditioner before diagnosing the breast cancer.

Desirably, as another example of the breast cancer diagnoser (FIG. 6C), a subtracter to obtain a per-pixel difference image between two thermographic images of the breast portion obtained with a time difference, a breast displacement energy calculator which calculates a breast displacement energy by a sum of squares of absolute values of all pixels of the difference image, and a tumor determiner (not illustrate) to determine the presence of tumor when the breast displacement energy is larger than a predetermined size may be included.

Since the larger the tumor, the larger the difference between two thermographic images so that the difference of the subtracter is increased and the breast displacement energy value is also increased.

Desirably, as still another example of the breast cancer diagnoser (FIG. 6C), it is determined whether the patient has breast cancer by a subtracter to obtain a per-pixel difference image between two thermographic images of the breast portion obtained with a time difference, a breast displacement energy calculator which calculates a breast displacement energy by a sum of squares of absolute values of all pixels of the difference image, a breast displacement graph generator which generates a breast displacement progress graph image showing the progress and the change of the breast displacement energy according to a time, and an artificial intelligence neural network which is trained in advance by the breast displacement graph images marked with a breast cancer patient and a normal patient. The time difference interval is preferably one month to six months.

FIGS. 7A and 7B are other examples of a breathing image recognizer 16e, which recognizes a temperature change according to breathing using thermographic images 79a and 79b in the vicinity of the mouth and the nose obtained by the body map mapper 4 from the thermographic video images 80a and 80b. Reference numeral 80b denotes a thermographic image obtained a time $\Delta t$ later after obtaining the thermographic image denoted by the reference numeral 80a.

Reference numeral 79b denotes a thermographic image in the vicinity of the mouth, and the nose obtained a time $\Delta t$ later after obtaining the thermographic image denoted by the reference numeral 79a.

When the patient breaths during an interval of a time $\Delta t$, a temperature change in the vicinity of the mouth and the nose of the patient is inevitable, and thus the breathing image recognizer 16e recognizes the temperature change.

In an example, the breathing image recognizer 16e of FIG. 7A may calculate a cough energy by a subtracter 78a to obtain a per-pixel difference image $(x(t)=l(t)-(l(t+\Delta t))$ between two thermographic images 79a and 79b in the vicinity of the mouth and the nose obtained with a time interval $\Delta t$ and a sum $(\Sigma |x(t)|^2)$ of squares of absolute values of all pixels of the difference image. Further, when the cough energy is larger than a predetermined threshold value, the cough determiner 83c may determine the presence of cough. When the cough energy is equal to or higher than a predetermined threshold value, the cough determiner 83c may provide a thermographic cough generation determining signal to the controller 60.

For example, since the larger the cough, the higher the air temperature change in the vicinity of the mouth and the nose so that the difference of the subtracter 83a is increased and the cough energy value is also increased.

In the present example, when the presence of the cough is determined, the controller 60 preferably accumulatively manages it to measure the frequency thereof to measure the risk of viral infection, the body temperature recognizer 16h more preferably measures the risk of viral infection of the patient by merging the information about the risk level of the disease infection, and most preferably measures the risk of the viral infection of the patient by reflecting and combining the sore throat test result.

Desirably, in the present disclosure, when the body temperature of the patient is 37.5 degrees or higher, the risk level of the disease infection is preferably assumed to be dangerous.

In an example, in the present disclosure, when the presence of cough of the patient is determined, it is accumulatively managed, and if the frequency of the cough is 10 or more per hour based on the detention period of the ceiling AI health monitoring apparatus of the patient, the risk of the viral infection is preferably assumed to be dangerous.

Further, in the present disclosure, when the frequency of the breathing of the patient during the sleeping is twenty times per minute or less, it is preferably determined to show the risk of dyspnea.

For example, according to still another aspect of the measurement of the risk level of the viral infection, the controller 60 finally determines whether the cough is generated by combining the cough determining signal provided by the coughing sound recognizer 16c illustrated in FIG. 8B and a thermographic cough generation determining signal provided by the coughing image recognizer 16d.

In this case, the controller 60 determines whether the cough is generated by combining two signals to improve the reliability of determining whether the cough is generated.

In an example, the controller 60 determines the sleep apnea syndrome and, when it is determined that the dyspnea occurs, may provide (report) the state of the patient by automatically making a call (auto dialing) to a predetermined emergency contact number or an emergency room (emergency center) such as 119 or 911 through the digital communication module 8. For example, the emergency contact number may be a contact number of acquaintances or relatives. Further, the controller 60 further includes a memory (not illustrated), and the memory (not illustrated) may be supplied with the emergency contact numbers stored through an application installed in the mobile phone (user terminal) or the like of the patient 88 using Bluetooth to store the emergency contact numbers.

Desirably, another aspect of the coughing image recognizer 16d may determine whether the cough of the patient occurs by the subtracter 78a, which generates a difference image to calculate a temperature change of the air in the vicinity of the mouth and the nose between two thermographic images 82a and 82b with a time difference, obtained by the body map mapper 4 and the artificial intelligence neural network which is trained in advance by the difference images obtained during the coughing of the patient.

According to another example of the present disclosure, a ceiling AI health monitoring system may be the same as or correspond to the above-described ceiling AI health monitoring apparatus 40. Accordingly, even though it is omitted, the contents described for the ceiling AI health monitoring apparatus 40 may also be applied to the description of the ceiling AI health monitoring system in the same way.

For example, the ceiling AI health monitoring system may include a monitoring device and a medical management device.

In an example, the monitoring device is provided on a ceiling of a space where the patient is located to acquire health information of the patient collected from a plurality of units. For example, the plurality of units may include a thermal imaging camera 22, a microphone 6, an IoT sensor, a user terminal, a wearable terminal, and the like, but is not limited thereto. As another example, the health information of the patient may include information such as a thermographic image, voice data, a body temperature, the number of steps, sleeping hours, a heart rate, a pulse, blood flow (blood volume), an electrocardiogram, and an exercise volume.

Further, the monitoring device may include a thermographic image acquirer, a microphone 6, a speaker 2, and a digital communication module 8, but is not limited thereto. For example, the monitoring device may be accommodated in the ceiling type main body 1a, 1b, and 1c to be concealed, or buried to be assembled, to be fixed, but is not limited thereto.

Further, the thermographic image acquirer may acquire body image information of the patient using the thermal imaging camera 22. For example, the thermal imaging camera 22 is provided (installed) above a bed in the space where the patient is located to acquire the patient's body image information.

Further, the microphone 6 may receive voice data, including a coughing sound and a breathing sound of the patient. Further, the microphone 6 may receive a voice command of the patient.

Further, the speaker 2 may output remote medical diagnosis information supplied from the doctor monitor 200 as a voice. The remote medical diagnosis information may include videos, images, texts, and voice data. The monitoring device may output information in accordance with the type of data in different manners. For example, in the case of data such as videos, images, and texts, the remote medical diagnosis information may be output to the user terminal (mobile phone).

Further, the digital communication module 8 may provide information acquired by the thermographic image acquirer and the microphone 6 to the medical management device. The digital communication module 8 may transmit body image information and voice data of the patient to the medical management device over a network.

In an example, the medical management device may apply the health information of the patient provided from the monitoring device to an artificial intelligence-based learning model to determine the health condition information of the patient. Further, the medical management device may provide the determination result to the doctor monitor of the medical specialist. Further, the medical equipment may provide the remote medical diagnosis information provided from the doctor monitor to the user terminal (mobile phone).

The medical management device may include a learner, a determiner, and a predicter, but the configuration of the medical management device is not limited thereto. The learner and the determiner may be the artificial intelligence neural network module 16, which has been described above. The artificial intelligence-based learning model to be described below may be a deep learning model, but is not limited thereto and may apply various neural network systems that have been developed or will be developed in the future.

Further, the learner may build a learning model by applying a plurality of learning medical data to the artificial intelligence model. The plurality of learning medical data may include data collected from big data, a hospital server, and a plurality of ceiling AI health monitoring apparatus 40.

Further, the determiner may determine the health condition information of the patient by applying the health information of the patient provided from the monitoring device 40 to the artificial intelligence-based learning model. In other words, the determiner inputs new data (health information of the patient) to a learning model built based on a plurality of data to determine the health condition information of the patient. Here, the health information of the patient may include body image information and voice data information of the patient acquired from the thermal imaging camera 22. Further, the health condition information of the patient, which is an output result of the learning model, may include information on whether the patient has a disease and a risk of the disease. In other words, as an output result of the learning model, information about whether the patient has a disease and the risk of the disease may be generated.

Further, the determiner may include a breathing state determiner and a coughing state determiner. The breathing state determiner to be described below may include a breathing sound recognizer 16b, the breathing image recognizer 16e, the sleep sensor 18, and the body temperature recognizer 16h, which have been described above. Further, the coughing state determiner may include a coughing sound recognizer 16c and a coughing image recognizer 16d.

For example, the breathing state determiner applies voice data received from the microphone 6 to the breathing sound learning model to determine a breathing state of the patient. In this case, the learner may build a breathing sound learning model with a breathing database for learning, including a plurality of breathing sounds among a plurality of learning medical data as an input of the artificial intelligence model. In other words, data included in the breathing database for learning is input to the artificial intelligence neural network to build a breathing sound learning model to determine whether the patient breaths.

As another example, the breathing state determiner may determine the patient's sleeping state information based on the patient's breathing state determined by being applied to the breathing sound learning model. Here, the patient's sleeping state information may include sleep apnea syndrome and dyspnea.

As another example, the breathing state determiner may include a subtracter, a breathing energy calculator, and a breathing determiner. For example, the subtracter 78a may obtain a per-pixel difference image between a plurality of thermographic images in the vicinity of the mouth and the nose acquired by the thermographic image acquirer with a predetermined time interval. The subtracter 78a may generate a per-pixel difference image $(x(t))=l(t)-(l(t+\Delta t))$ between two thermographic images 79a and 79b in the vicinity of the mouth and the nose acquired with a time interval of $\Delta t$. Further, the breathing energy calculator may calculate the breathing energy by a sum of squares for absolute values of all pixels of the difference image. In the meantime, the breathing energy calculator may calculate the cough energy from a sum of squares for absolute values of all pixels of the difference image. The breathing determiner may determine the presence of the breathing when the breathing energy is equal to or higher than a predetermined reference value. Further, the breathing determiner may determine the presence of the coughing when the cough energy is equal to or higher than a predetermined reference value.

Further, the coughing state determiner applies voice data received from the microphone 6 to the coughing sound learning model to determine a coughing state of the patient. The coughing state determiner may determine the coughing state of the patient in connection with whether the patient coughs due to aspiration, or due to the cold, or due to the pandemic (corona), based on the voice data (coughing data) of the patient which is newly input. In this case, the learner may build a coughing sound learning model with a learning coughing database configured by a plurality of coughing sounds among a plurality of learning medical data as an input of the artificial intelligence model. In other words, data included in the learning coughing database is input to the artificial intelligence neural network to build a coughing sound learning model to determine the coughing state of the patient.

Further, the learner may build the coughing image learning model with learning thermal imaging medical data, including a temperature distribution and a temperature value of a facial portion of the patient among the plurality of learning medical data as an input of the artificial intelligence model. In this case, the coughing state determiner applies the plurality of thermographic images representing the temperature change in the air in the vicinity of the mouth and the nose acquired from the thermal imaging camera 22 to the coughing image learning model to determine whether the patient coughs.

Further, the predicter may predict the risk of viral infection based on the information regarding the breathing state or the coughing state of the patient, which is a learning result of the breathing sound learning model and the coughing sound learning model and information of whether the patient coughs which is a learning result of the coughing image learning model.

In an example, the medical management device may determine whether the patient has breast cancer. The medical management device may include a subtracter, a breast displacement energy calculator, a breast displacement graph generator, and a breast cancer diagnoser (FIG. 6C). For example, the subtracter may calculate the per-pixel difference image between the plurality of thermographic images of the breast portion acquired by the thermographic image acquirer with a predetermined time interval. The breast displacement energy calculator may calculate the breast displacement energy from a sum of squares for absolute values of all pixels of the difference image. The breast displacement graph generator may generate a breast displacement progress graph image representing progress and a change of the breast displacement energy according to a time. Further, the breast cancer diagnoser (FIG. 6C) may determine whether the patient has breast cancer using an artificial intelligence neural network which is built with the plurality of breast displacement progress graph images respectively marked with a breast cancer patient or a normal patient as an input.

In an example, the medical management device may use the sleep sensor 18 to determine that the patient is sleeping when an accumulated value of the sound energy included in the patient's health information is equal to or lower than a predetermined reference value or an accumulated value of the motion changing energy of the patient is equal to or lower than a predetermined reference value.

FIG. 9 is an example showing a remote medical diagnosis method that tests sore throat by utilizing a ceiling AI health monitoring apparatus 40 according to the present disclosure.

In an example, the remote diagnosis method which tests sore throat by utilizing the ceiling AI health monitoring apparatus 40 may include an operation of authenticating a patient by any one method selected from face recognition, finger recognition, iris recognition, voice recognition, ID authentication, and authentication through a mobile device. Further, the remote medical diagnosis method, which tests sore throat by utilizing the ceiling AI health monitoring apparatus 40, may include an operation of capturing an image picture 10a of tonsil and uvula in the mouth using a mobile phone camera 89 by the patient 88.

Further, the remote medical diagnosis method which tests sore throat by utilizing the ceiling AI health monitoring apparatus 40 may include an operation of displaying the captured image picture 10a on the screen displayer 10 and transmitting the captured image picture to the medical data receiver 12 of the ceiling AI health monitoring apparatus 40. Further, the remote medical diagnosis method which tests sore throat by utilizing the ceiling AI health monitoring apparatus 40 may include an operation of analyzing the image picture 10a received by the medical data receiver 12 to diagnose the sore throat of the patient by the artificial intelligence neural network module 16, transmitting information displayed on the screen displayer 10 to the doctor monitor 200 by means of the communication server 203 and the communication network 202, and allowing the doctor 201 to help the self-diagnosis of the patient 88 while observing the information on the monitor 200 in real-time. In this case, information displayed on the screen displayer 10 and information that the doctor watches on the monitor 200 are the same so that the doctor 201 may easily help the patient 88.

Further, the doctor 201 shares the information through the monitor 200 in real-time so that the doctor may directly instruct the patient to correct the posture of the mobile phone camera 89 through the communication network 202 using the voice so that the doctor may help the patient self-diagnosis as if the doctor is next to the patient.

The reference numeral 59b is an example indicating that an image obtained by the mobile phone camera 89 is simultaneously displayed on the monitor 200 of the doctor 201.

Desirably, the remote medical diagnosis method for discovering a viral infection risk group by utilizing a ceiling AI health monitoring apparatus 40 according to the present disclosure may include an operation of requesting a patient to give a control right of the ceiling AI health management apparatus 40 by a disease management authority.

Further, the remote medical diagnosis method for discovering a viral infection risk group by utilizing a ceiling AI health monitoring apparatus 40 may include an operation of transferring the control right of the ceiling AI health monitoring apparatus to a disease management authority via a predetermined authentication procedure, by means of a computer app or a mobile app, by a patient.

Further, the remote medical diagnosis method for discovering a viral infection risk group by utilizing a ceiling AI health monitoring apparatus 40 may include an operation of controlling or using the ceiling AI health monitoring apparatus 40 by means of the digital communication module 8, by the disease management authority which receives the control right.

Further, the remote medical diagnosis method for discovering a viral infection risk group by utilizing a ceiling AI health monitoring apparatus 40 may include an operation of directly transmitting a health management guideline to the patient 88 by means of the microphone 6 and the screen displayer 10, by the disease management authority.

Further, the remote medical diagnosis method for discovering a viral infection risk group by utilizing a ceiling AI health monitoring apparatus 40 may include an operation of checking a body temperature, sore throat, and a coughing state of the patient by means of the remote diagnosis, by the disease management authority.

Further, the remote medical diagnosis method for discovering a viral infection risk group by utilizing a ceiling AI health monitoring apparatus 40 may include an operation of checking (determining) the abnormality of the patient, based on the body temperature, the sore throat test, the dyspnea or the coughing state of the patient to report the abnormality to the disease management authority when the patient has a symptom.

Further, the remote medical diagnosis method for discovering a viral infection risk group by utilizing a ceiling AI health monitoring apparatus 40 may include an operation of reading recent health history information of the patient stored in the ceiling AI health monitoring apparatus 40.

In an example, an example of a remote medical diagnosis method that tests viral infection by utilizing a ceiling AI health monitoring apparatus 40 may include an operation of visiting a suspected patient to distribute a virus diagnosis kit by the disease management authority.

Further, the remote medical diagnosis method for testing a viral infection by utilizing a ceiling AI health monitoring apparatus 40 according to the present disclosure, may include an operation of transferring a control right of the ceiling AI health monitoring apparatus 40 to a disease management authority from the patient.

Further, the remote medical diagnosis method for testing a viral infection by utilizing a ceiling AI health monitoring apparatus 40 may include an operation of providing training on how to use a virus diagnosis kit to the suspected patient using the microphone 6 and the screen displayer 10, by means of remote medical diagnosis, by the disease management authority.

Further, the remote medical diagnosis method for testing a viral infection by utilizing a ceiling AI health monitoring apparatus 40 may include an operation of capturing a diagnosis result of the virus diagnosis kit obtained by using its own sample of the patient with a mobile phone camera to transmit the result to the medical data receiver 12 of the ceiling AI health monitoring apparatus 40.

Further, the remote medical diagnosis method for testing a viral infection by utilizing a ceiling AI health monitoring apparatus 40 may include an operation of remotely reading the diagnosis result of the virus diagnosis kit from the ceiling AI health monitoring apparatus 40 by the disease management authority to determine whether the patient is normal.

The remote medical diagnosis method using the ceiling AI health monitoring apparatus according to an example of the present disclosure may be implemented as a program command, which may be executed by various computers to be recorded in a computer-readable medium. The computer-readable medium may include solely a program instruction, a data file, and a data structure or a combination thereof. The program instruction recorded in the medium may be specifically designed or constructed for the present invention or known to those skilled in the art of computer software to be used. Examples of the computer-readable recording medium include a magnetic media such as a hard disk, a floppy disk, or a magnetic tape, an optical media such as a CD-ROM or a DVD, a magneto-optical media such as a floptical disk, and a hardware device which is specifically configured to store and execute the program instruction, such as a ROM, a RAM, or a flash memory. Examples of the program instruction include not only a machine language code that is created by a compiler but also a high-level language code that may be executed by a computer using an interpreter. The hardware device may operate as one or more software modules in order to perform the operation of the present invention and vice versa.

Further, the above-described remote medical diagnosis method using the ceiling AI health monitoring apparatus may also be implemented as a computer program or an application executed by a computer that is stored in a recording medium.

The image display apparatus described herein may be implemented using a liquid crystal display (LCD), a light-emitting diode (LED) display, a plasma display panel (PDP), a screen, a terminal, or any other type of display configured to display the images and information to be displayed by the image display apparatus. A screen may be a physical structure that includes one or more hardware components that provide the ability to render a user interface and receive user input. The screen may include any combination of a display region, a gesture capture region, a touch-sensitive display, and a configurable area. The screen may be part of an apparatus, or may be an external peripheral device that is attachable to and detachable from the apparatus. The display may be a single-screen display or a multi-screen display. A single physical screen may include multiple displays that are managed as separate logical displays permitting different content to be displayed on separate displays even though they are part of the same physical screen.

The user interface may provide the capability of inputting and outputting information regarding a user and an image. The user interface may include a network module for connecting to a network and a universal serial bus (USB) host module for forming a data transfer channel with a mobile storage medium. In addition, the user interface may include one or more input/output devices, such as a mouse, a keyboard, a touch screen, a monitor, a speaker, a screen, or a software module for controlling the input/output device.

The ceiling AI health monitoring apparatus, body map mapper, body temperature recognizer, thermographic image acquirer, learner, determiner, predicter, calculator, generator, diagnoser, sensor, recognizer, analyzer, displayer, converter, commander, and transmitter in FIGS. 1-9 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-9 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A ceiling artificial intelligence (AI) health monitoring system, comprising:
    a monitoring device disposed on a ceiling of a space to acquire health information from a patient; and
    a medical management device configured to apply the health information of the patient to an artificial intelligence-based learning model to determine health condition information of the patient and to provide a determination result to a doctor monitor,
    wherein the medical management device is further configured to provide remote medical diagnosis information from the doctor monitor to a user terminal,
    wherein the monitoring device comprises a thermographic image acquirer configured to acquire body image information of the patient using a thermal imaging camera, and
    wherein the medical management device comprises a breathing state determiner comprising
        a subtracter configured to obtain a per-pixel difference image between a plurality of thermographic images in a vicinity of a mouth and a nose acquired by the thermographic image acquirer with a predetermined time interval;
        a breathing energy calculator configured to calculate a breathing energy by a sum of squares of absolute values of all pixels of the per-pixel difference image; and
        a breathing determiner configured to determine a presence of breath when the breathing energy is equal to or higher than a threshold value.

2. The ceiling AI health monitoring system of claim 1, wherein the monitoring device comprises:
a microphone configured to acquire voice data including a coughing sound and a breathing sound of the patient;
a speaker configured to output the remote medical diagnosis information as speech; and
a digital communication module configured to provide the body image information and the voice data to the medical management device.

3. The ceiling AI health monitoring system of claim 2, wherein the medical management device comprises:
a learner configured to apply a plurality of learning medical data to an artificial intelligence model to build a learning model; and
the determiner configured to determine the health condition information by applying the health information to the artificial intelligence-based learning model, wherein
the health condition information includes information of whether the patient has a disease and a risk of the disease.

4. The ceiling AI health monitoring system of claim 3, wherein the determiner further comprises:
the breathing state determiner is further configured to determine a breathing state of the patient by applying the voice data to a breathing sound learning model; and
a coughing state determiner configured to determine a coughing state of the patient by applying the voice data to a coughing sound learning model,
wherein the learner is further configured to build a breathing sound learning model with a breathing database including a plurality of breathing sounds, among a plurality of learning medical data, as an input of the artificial intelligence model, and to build a coughing sound learning model with a coughing database including a plurality of coughing sounds, among the plurality of learning medical data, as the input of the artificial intelligence model.

5. The ceiling AI health monitoring system of claim 4, wherein the learner is further configured to build a coughing image learning model with thermographic medical data including a temperature distribution and a temperature value of a facial portion of the patient among the plurality of medical data for learning as the input of the artificial intelligence model, and the coughing state determiner is further configured to apply a plurality of thermographic images representing an air temperature change in a vicinity of a mouth and a nose acquired from the thermal imaging camera to the coughing image learning model to determine whether the patient coughs.

6. The ceiling AI health monitoring system of claim 5, wherein the medical management device further comprises a predicter configured to predict a risk of viral infection based on the breathing state or the coughing state of the patient which is a learning result of the breathing sound learning model and the coughing sound learning model and information indicating whether the patient coughs which is a learning result of the coughing image learning model.

7. The ceiling AI health monitoring system of claim 4, wherein the breathing state determiner is further configured to determine sleeping state information of the patient based on a breathing state information determined based on the breathing sound learning model and the sleeping state information including sleep apnea and dyspnea.

8. The ceiling AI health monitoring system of claim 2, wherein the medical management device further comprises:
a subtracter configured to calculate a per-pixel difference image between a plurality of thermographic images of a breast portion acquired by the thermographic image acquirer with a predetermined time interval;
a breast displacement energy calculator configured to calculate a breast displacement energy by a sum of squares of absolute values of all pixels of the per-pixel difference image;
a breast displacement graph generator configured to generate a breast displacement progress graph image representing a progress and a change of the breast displacement energy over time; and
a breast cancer diagnoser configured to determine whether the patient has breast cancer using an artificial intelligence neural network built with a plurality of breast displacement progress graph images marked with a breast cancer patient or a normal patient as an input.

9. The ceiling AI health monitoring system of claim 1, wherein the medical management device further comprises:
a sleep sensor configured to determine the patient is sleeping when an accumulated value of a sound energy included in the health information of the patient is equal to or lower than a predetermined reference value or an accumulated value of a motion changing energy of the patient is equal to or lower than a predetermined reference value.

10. An artificial intelligence (AI) health monitoring system, comprising:
a monitoring device disposed on a ceiling of a space to acquire health information from a patient; and
a medical management device configured to apply the health information of the patient acquired by an artificial intelligence-based learning model to determine health condition information of the patient, to provide a determination result to a doctor monitor, and to provide remote medical diagnosis information from the doctor monitor to a user terminal,
wherein the monitoring device comprises a thermographic image acquirer configured to acquire body image information of the patient using a thermal imaging camera, and
wherein the medical management device comprises
a subtracter configured to calculate a per-pixel difference image between a plurality of thermographic images of a breast portion acquired by the thermographic image acquirer with a predetermined time interval;
a breast displacement energy calculator configured to calculate a breast displacement energy by a sum of squares of absolute values of all pixels of the per-pixel difference image;
a breast displacement graph generator configured to generate a breast displacement progress graph image representing a progress and a change of the breast displacement energy over time; and
a breast cancer diagnoser configured to determine whether the patient has breast cancer using an artificial intelligence neural network built with a plurality of breast displacement progress graph images marked with a breast cancer patient or a normal patient as an input.

* * * * *